(12) United States Patent
Logan et al.

(10) Patent No.: US 6,699,256 B1
(45) Date of Patent: Mar. 2, 2004

(54) MEDICAL GRAFTING APPARATUS AND METHODS

(75) Inventors: John Logan, Plymouth, MN (US); Scott Thome, St. Cloud, MN (US); Alex Peterson, Maple Grove, MN (US); Todd A. Berg, Plymouth, MN (US)

(73) Assignee: St. Jude Medical ATG, Inc., Maple Grove, MN (US)

( * ) Notice: Subject to any disclaimer, the term of this patent is extended or adjusted under 35 U.S.C. 154(b) by 17 days.

(21) Appl. No.: 09/587,112

(22) Filed: Jun. 2, 2000

Related U.S. Application Data

(60) Provisional application No. 60/137,764, filed on Jun. 4, 1999.

(51) Int. Cl.[7] .......................... A61B 17/08; A61B 17/32
(52) U.S. Cl. ........................................ 606/153; 606/184
(58) Field of Search .......................... 606/151–155, 606/184, 185, 186

(56) References Cited

U.S. PATENT DOCUMENTS

| | | | |
|---|---|---|---|
| 3,796,211 A | 3/1974 | Kohl | 128/2 B |
| 3,867,945 A | 2/1975 | Long | 128/349 R |
| 3,903,892 A | 9/1975 | Komiya | 128/334 R |
| 4,214,587 A | 7/1980 | Sakura, Jr. et al. | 128/334 R |
| 4,418,693 A | 12/1983 | LeVeen et al. | 128/303 R |
| 4,459,252 A | 7/1984 | MacGregor | 264/46.9 |
| 4,470,415 A | 9/1984 | Wozniak | 128/334 R |
| 4,503,569 A | 3/1985 | Dotter | 3/1.4 |
| 4,545,390 A | 10/1985 | Leary | 128/772 |
| 4,592,754 A | 6/1986 | Gupte et al. | 623/1 |
| 4,605,406 A | 8/1986 | Cahalan et al. | 623/1 |
| 4,617,932 A | 10/1986 | Kornberg | 128/334 R |
| 4,629,458 A | 12/1986 | Pinchuk | 623/1 |
| 4,632,842 A | 12/1986 | Karwoski et al. | 427/2 |
| 4,651,733 A | 3/1987 | Mobin-Uddin | 128/303 R |
| 4,665,906 A | 5/1987 | Jervis | 128/92 YN |
| 4,705,517 A | 11/1987 | DiPisa, Jr. | 623/12 |

(List continued on next page.)

FOREIGN PATENT DOCUMENTS

| | | | |
|---|---|---|---|
| AU | 670239 | 1/1994 | A61F/2/06 |
| DE | 4404806 C1 | 2/1995 | A61B/17/22 |
| EP | 539237 A1 | 4/1993 | A61F/2/06 |
| EP | 637454 A1 | 2/1995 | A61M/25/10 |
| EP | 680734 A2 | 11/1995 | A61F/2/06 |
| EP | 684022 A2 | 11/1995 | A61F/2/06 |
| EP | 701800 A1 | 3/1996 | A61F/2/06 |
| EP | 712614 A1 | 5/1996 | A61F/2/06 |
| EP | 723786 A1 | 7/1996 | A61M/25/00 |

(List continued on next page.)

*Primary Examiner*—Michael J. Milano
*Assistant Examiner*—Jessica R Baxter
(74) *Attorney, Agent, or Firm*—Fish & Neave; Robert R. Jackson; Jeffrey C. Aldridge

(57) ABSTRACT

Instrumentation for facilitating cutting an opening in a side wall of a body conduit in a patient. A tubular structure defines a lumen and has a sharpened distal end portion configured to cut a section of the body conduit to create the opening. A tissue holding structure is provided which is axially movable within the lumen of the tubular structure. The tissue holding structure includes a piercing portion to permit passage of the tissue holding structure through the body conduit from an entrance side to an exit side thereof. The tissue holding structure also includes a retention member to secure the section of the body conduit to the tissue holding structure during movement of the tissue holding structure to approximate the entrance side of the body conduit with the sharpened distal portion of the tubular structure to enable the sharpened distal structure to cut the body conduit. A connector is also provided for attaching a new length of tubing to the body conduit at the opening made by the cutting.

33 Claims, 22 Drawing Sheets

U.S. PATENT DOCUMENTS

| | | | | |
|---|---|---|---|---|
| 4,718,907 | A | 1/1988 | Karwoski et al. | 623/12 |
| 4,733,665 | A | 3/1988 | Palmaz | 128/343 |
| 4,738,740 | A | 4/1988 | Pinchuk et al. | 156/167 |
| 4,743,252 | A | 5/1988 | Martin, Jr. et al. | 623/1 |
| 4,748,984 | A | 6/1988 | Patel | 128/658 |
| 4,787,899 | A | 11/1988 | Lazarus | 623/1 |
| 4,795,458 | A | 1/1989 | Regan | 623/1 |
| 4,798,606 | A | 1/1989 | Pinchuk | 623/1 |
| 4,892,539 | A | 1/1990 | Koch | 623/1 |
| 4,911,163 | A | 3/1990 | Fina | 606/127 |
| 4,969,890 | A | 11/1990 | Sugita et al. | 606/192 |
| 5,035,702 | A | 7/1991 | Taheri | 606/153 |
| 5,037,377 | A | 8/1991 | Alonso | 600/36 |
| 5,061,245 | A | 10/1991 | Waldvogel | 604/170 |
| 5,061,275 | A | 10/1991 | Wallsten et al. | 623/1 |
| 5,084,065 | A | 1/1992 | Weldon et al. | 623/1 |
| 5,104,399 | A | 4/1992 | Lazarus | 623/1 |
| 5,116,360 | A | 5/1992 | Pinchuk et al. | 623/1 |
| 5,122,154 | A | 6/1992 | Rhodes | 606/198 |
| 5,122,156 | A | 6/1992 | Granger et al. | 606/219 |
| 5,135,467 | A | 8/1992 | Citron | 600/16 |
| 5,147,370 | A | 9/1992 | McNamara et al. | 606/108 |
| 5,163,951 | A | 11/1992 | Pinchuk et al. | 623/1 |
| 5,171,233 | A | 12/1992 | Amplatz et al. | 604/281 |
| 5,201,901 | A | 4/1993 | Harada et al. | 606/198 |
| 5,207,695 | A | 5/1993 | Trout, III | 606/153 |
| 5,209,731 | A | 5/1993 | Sterman et al. | 604/97 |
| 5,211,658 | A | 5/1993 | Clouse | 623/1 |
| 5,211,683 | A | 5/1993 | Maginot | 128/898 |
| 5,226,429 | A | 7/1993 | Kuzmak | 128/898 |
| 5,234,447 | A | 8/1993 | Kaster et al. | 606/153 |
| 5,256,150 | A | 10/1993 | Quiachon et al. | 604/171 |
| 5,275,622 | A | 1/1994 | Lazarus et al. | 623/1 |
| 5,287,861 | A | 2/1994 | Wilk | 128/898 |
| 5,297,564 | A | 3/1994 | Love | 128/898 |
| 5,304,220 | A | 4/1994 | Maginot | 623/1 |
| 5,306,240 | A | 4/1994 | Berry | 604/51 |
| 5,316,023 | A | 5/1994 | Palmaz et al. | 128/898 |
| 5,330,500 | A | 7/1994 | Song | 606/198 |
| 5,334,217 | A | 8/1994 | Das | 606/213 |
| 5,354,309 | A | 10/1994 | Schnepp-Pesch et al. | 606/198 |
| 5,354,336 | A | 10/1994 | Kelman et al. | 623/6 |
| 5,360,443 | A | 11/1994 | Barone et al. | 623/1 |
| 5,366,441 | A | 11/1994 | Crawford | 604/53 |
| 5,366,504 | A | 11/1994 | Anderson et al. | 623/11 |
| 5,387,235 | A | 2/1995 | Chuter | 623/1 |
| 5,395,349 | A | 3/1995 | Quiachon et al. | 604/248 |
| 5,397,345 | A | 3/1995 | Lazarus | 623/1 |
| 5,397,355 | A | 3/1995 | Marin et al. | 623/12 |
| 5,409,019 | A | 4/1995 | Wilk | 128/898 |
| 5,419,324 | A | 5/1995 | Dillow | 128/653.1 |
| 5,425,765 | A | 6/1995 | Tiefenbrun et al. | 623/12 |
| 5,429,144 | A | 7/1995 | Wilk | 128/898 |
| 5,433,727 | A | 7/1995 | Sideris | 606/213 |
| 5,437,288 | A | 8/1995 | Schwartz et al. | 128/772 |
| 5,443,497 | A | 8/1995 | Venbrux | 623/1 |
| 5,443,499 | A | 8/1995 | Schmitt | 623/1 |
| 5,452,733 | A | 9/1995 | Sterman et al. | 128/898 |
| 5,456,712 | A | 10/1995 | Maginot | 623/1 |
| 5,470,320 | A | 11/1995 | Tiefenbrun et al. | 604/174 |
| 5,480,423 | A | 1/1996 | Ravenscroft et al. | 623/1 |
| 5,484,418 | A | 1/1996 | Quiachon et al. | 604/167 |
| 5,488,958 | A | 2/1996 | Topel et al. | 128/754 |
| 5,489,295 | A | 2/1996 | Piplani et al. | 623/1 |
| 5,496,365 | A | 3/1996 | Sgro | 623/1 |
| 5,507,769 | A | 4/1996 | Marin et al. | 606/198 |
| 5,509,931 | A | 4/1996 | Schmitt | 623/1 |
| 5,522,834 | A | 6/1996 | Fonger et al. | 606/194 |
| 5,522,880 | A | 6/1996 | Barone et al. | 623/1 |
| 5,522,882 | A | 6/1996 | Gaterud et al. | 623/1 |
| 5,542,944 | A | 8/1996 | Bhatta | 606/33 |
| 5,545,214 | A | 8/1996 | Stevens | 623/2 |
| 5,549,663 | A | 8/1996 | Cottone, Jr. | 623/1 |
| 5,554,152 | A | 9/1996 | Aita et al. | 606/7 |
| 5,562,725 | A | 10/1996 | Schmitt et al. | 623/1 |
| 5,562,728 | A | 10/1996 | Lazarus et al. | 623/1 |
| 5,571,167 | A | 11/1996 | Maginot | 623/1 |
| 5,571,172 | A | 11/1996 | Chin | 623/1 |
| 5,571,215 | A | 11/1996 | Sterman et al. | 623/66 |
| 5,584,875 | A | 12/1996 | Duhamel et al. | 623/1 |
| 5,628,786 | A | 5/1997 | Banas et al. | 623/1 |
| 5,628,788 | A | 5/1997 | Pinchuk | 623/1 |
| 5,632,772 | A | 5/1997 | Alcime et al. | 623/1 |
| 5,653,747 | A | 8/1997 | Dereume | 623/1 |
| 5,676,670 | A | 10/1997 | Kim | 606/108 |
| 5,690,662 | A | 11/1997 | Chiu et al. | 606/184 |
| 5,693,083 | A | 12/1997 | Baker et al. | 623/1 |
| 5,695,504 | A | * 12/1997 | Gifford et al. | 606/153 |
| 5,702,412 | A | 12/1997 | Popov et al. | 606/159 |
| 5,707,380 | A | 1/1998 | Hinchliffe et al. | 606/153 |
| 5,755,778 | A | 5/1998 | Kleshinski | 623/1 |
| 5,797,920 | A | 8/1998 | Kim | 606/108 |
| 5,827,316 | A | 10/1998 | Young et al. | 606/185 |
| 5,830,222 | A | 11/1998 | Makower | 606/159 |
| 5,843,164 | A | 12/1998 | Frantzen et al. | 623/1 |
| 5,843,170 | A | 12/1998 | Ahn | 623/1 |
| 5,843,175 | A | 12/1998 | Frantzen | 623/1 |
| 5,893,369 | A | 4/1999 | LeMole | 606/184 |
| 5,910,153 | A | 6/1999 | Mayenberger | 606/184 |
| 5,922,022 | A | 7/1999 | Nash et al. | 623/1 |
| 5,941,908 | A | 8/1999 | Goldsteen et al. | 623/1 |
| 5,951,576 | A | * 9/1999 | Wakabayashi | 606/151 |
| 5,972,017 | A | 10/1999 | Berg et al. | 606/198 |
| 5,976,178 | A | 11/1999 | Goldsteen et al. | 623/1 |
| 5,989,276 | A | * 11/1999 | Houser et al. | 606/139 |
| 6,001,124 | A | 12/1999 | Bachinski | 623/1 |
| 6,026,814 | A | 2/2000 | LaFontaine et al. | 128/898 |
| 6,030,392 | A | 2/2000 | Dakov | 606/139 |
| 6,035,856 | A | 3/2000 | LaFontaine et al. | 128/898 |
| 6,113,612 | A | 9/2000 | Swanson et al. | 606/153 |
| 6,152,937 | A | 11/2000 | Peterson et al. | 606/153 |
| 6,254,617 | B1 | * 7/2001 | Spence et al. | 606/153 |
| 6,254,618 | B1 | 7/2001 | Dakov | 606/153 |
| 6,293,955 | B1 | * 9/2001 | Houser et al. | 606/153 |
| 6,416,527 | B1 | 7/2002 | Berg et al. | 606/180 |
| 2001/0039425 | A1 | 11/2001 | Dakov | 606/153 |

FOREIGN PATENT DOCUMENTS

| | | | |
|---|---|---|---|
| EP | 732087 A1 | 9/1996 | A61F/2/06 |
| EP | 737453 A2 | 10/1996 | A61F/2/06 |
| EP | 807412 A1 | 11/1997 | A61B/17/32 |
| GB | 2269104 A | 2/1994 | A61F/2/06 |
| WO | WO 89/08433 | 9/1989 | A61F/2/04 |
| WO | WO 93/00868 | 1/1993 | A61F/2/06 |
| WO | WO 93/20757 | 10/1993 | A61B/17/11 |
| WO | WO 94/01056 | 1/1994 | A61F/2/04 |
| WO | WO 94/06372 | 3/1994 | A61F/2/04 |
| WO | WO 95/17127 | 6/1995 | A61B/17/11 |
| WO | WO 95/21592 | 8/1995 | A61F/2/06 |
| WO | WO 96/01591 | 1/1996 | A61B/17/22 |
| WO | WO 96/01599 | 1/1996 | A61F/2/06 |
| WO | WO 96/14808 | 5/1996 | A61F/2/02 |
| WO | WO 96/18361 | 6/1996 | A61F/2/06 |
| WO | WO 96/22745 | 8/1996 | A61F/2/06 |
| WO | WO 96/25897 | 8/1996 | A61F/2/06 |
| WO | WO 97/12555 | 4/1997 | A61B/17/11 |
| WO | WO 97/13463 | 4/1997 | A61B/17/00 |
| WO | WO 97/13471 | 4/1997 | A61B/19/00 |
| WO | WO 97/27893 | 8/1997 | A61M/19/00 |
| WO | WO 97/27897 | 8/1997 | A61M/29/00 |
| WO | WO 97/27898 | 8/1997 | A61M/29/00 |

| | | | | | | | |
|---|---|---|---|---|---|---|---|
| WO | WO 98/02099 | 1/1998 | ............ A61B/17/00 | WO | WO 98/38939 | 9/1998 | ............ A61B/19/00 |
| WO | WO 98/08456 | 3/1998 | ............ A61B/19/00 | WO | WO 98/38941 | 9/1998 | ............ A61B/19/00 |
| WO | WO 98/16161 | 4/1998 | ............ A61B/17/36 | WO | WO 98/42262 | 10/1998 | ............ A61B/17/04 |
| WO | WO 98/19618 | 5/1998 | ............ A61B/19/00 | WO | WO 99/38454 | 8/1999 | ............. A61F/2/06 |
| WO | WO 98/19629 | 5/1998 | ............. A61F/2/06 | | | | |
| WO | WO 98/19634 | 5/1998 | ............. A61F/2/06 | | | | |
| WO | WO 98/19635 | 5/1998 | ............. A61F/2/06 | | | | |

* cited by examiner

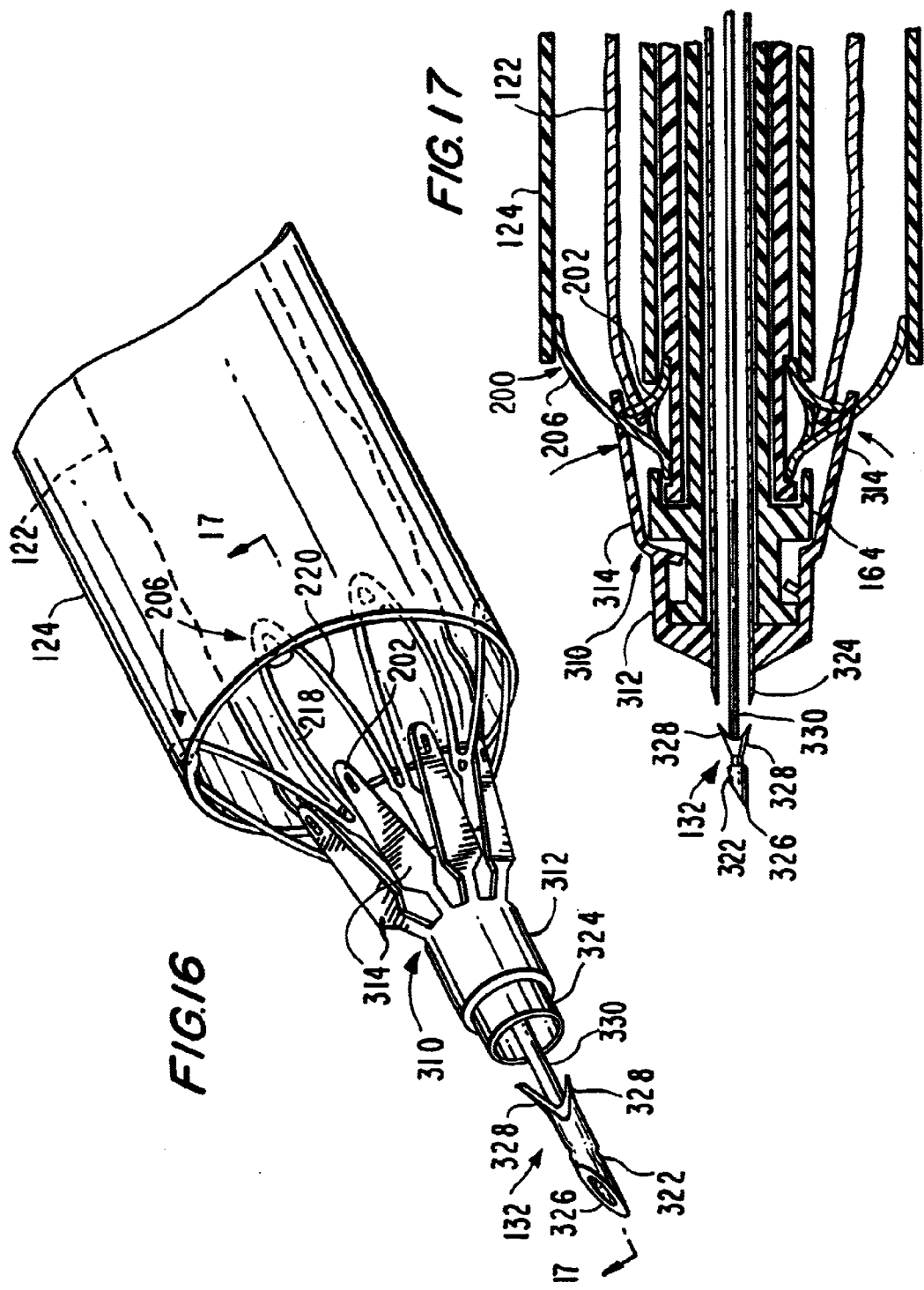

MEDICAL GRAFTING APPARATUS AND METHODS

This application claims the benefit of U.S. Provisional application Serial No. 60/137,764, filed Jun. 4, 1999, which is incorporated by reference in its entirety herein.

BACKGROUND OF THE INVENTION

This invention relates to medical methods and apparatus, and more particularly to methods and apparatus for installing a tubular graft in a patient for such purposes as bypassing an occlusion or narrowing in the patient's tubular body structure. More particularly, this invention relates to instrumentation and methods for providing an opening in a side wall of the patient's body structure, and instrumentation and methods for attaching the tubular graft to the patient's body structure at the opening that has been made.

The invention is applicable to making anastomotic connections between all body conduits. For example, the invention also has application for attaching coronary artery bypass grafts. Specifically, connection methods and apparatus are provided for attaching the graft ends to the coronary artery and the aortic artery. In the case of the internal mammary artery, connection is required at the coronary artery only.

During coronary bypass surgery vein grafts are attached to the ascending aorta, i.e., a proximal anastomosis, and to the coronary artery, i.e., a distal anastomosis. The vein graft bypasses the diseased or stenotic region of the coronary artery allowing blood to flow through the graft and perfuse the heart distal to the stenosis site.

An early step in the procedure is to create a hole in the artery to which the vein graft is to be connected. A precisely controlled hole and geometry is needed to optimize the performance of the anastomosis. According to conventional techniques, a scalpel and a punch are used. A slit is first made in the aortic wall. The slit is typically wider than the punch, such that the distal end of the punch can be inserted through the slit into the lumen of the artery. An aortic punch consists of an anvil portion and tube that are relatively movable with respect to each other. The aortic punch removes a portion of the wall by crushing or forcing the anvil section inside the artery lumen, against the tube positioned outside the artery wall. The compressive action of the anvil against the tube shears and crushes the tissue between the anvil and the tube.

The method has several disadvantages. The hole produced is typically very irregular and variable in size. Moreover, the initial scalpel slit, typically extends beyond the opening made by the aortic punch and ay result in leakage. The surrounding residual tissue, which has been left behind, is usually damaged due to the crushing action. This damage can produce a biological healing response for the damaged cells, which can cause inflammation and other adverse events at the critical anastomosis site.

The conventional procedure to make the connections after the hole has been made is by hand-sewing or suturing. It will be appreciated, however, that making such connections by suturing can be extremely difficult, time-consuming, and dependent on the skill of the physician for the quality of the results. There is also increasing interest in less invasive procedures which tend to impose constraints on the physician's access to the sites at which graft connections must be made and thereby make it more difficult or even impossible to use suturing to make such connections (see, for example, Goldsteen et al. U.S. Pat. No. 5,976,178, Sullivan et al. U.S. Pat. No. 6,120,432, Sullivan et al. U.S. patent application Ser. No. 08/869,808, filed Jun. 5, 1997, concurrently filed U.S. patent application Ser. No. 09/187,364, filed Nov. 6, 1998 and Peterson et al. U.S. Pat. No. 6,152,937, all of which are hereby incorporated by reference herein in their entireties). Conventional suturing techniques may contribute to the failure of the anastomosis. The sutures themselves may initiate injury to the graft vessel.

In view of the foregoing, it is an object of this invention to provide improved and simplified apparatus and methods for providing an opening in tubular body conduit.

It is still another object of this invention to provide improved and simplified methods of making structures that can be used as medical connector apparatus.

It is also an advantage of the invention to provide an improved and consistent anastomosis result, without the reliance on the technique and skill of the physician.

SUMMARY OF THE INVENTION

These and other objects of the invention are accomplished in accordance with the principles of the invention by providing improved apparatus and methods for installing a guide structure in a patient between two locations along the patient's circulatory system that are to be connected by a bypass graft.

Instrumentation is provided for facilitating cutting an opening in a side wall of a body conduit. A tubular structure is provided which defines a lumen and has a sharpened distal end portion configured to cut a section of the body conduit to create the opening. A tissue holding structure is also provided which is axially movable within the lumen of the tubular structure. The tissue holding structure includes a piercing portion to permit passage of the tissue holding structure through the body conduit from an entrance side adjacent the tubular structure to an exit side thereof. The tissue holding structure also includes a retention member to secure the body conduit to the tissue holding structure during movement of the tissue holding structure to approximate the entrance side of the section of the body conduit and the sharpened distal portion of the tubular structure which enables the sharpened distal end portion to cut the section of body conduit.

After the section of body conduit has been cut, the tissue holding structure and the section of body conduit secured thereto by the retention member are proximally movable into the lumen of the tubular structure.

In one embodiment, the retention member is a barb that is resiliently biased radially outwardly in order to secure the section of body conduit. The barb may be deflected radially inwardly during the distal passage of the tissue holding structure through the section of the body conduit.

The piercing portion may be a needle catheter having a sharpened distal end portion to permit distal passage of the tissue holding structure through the section of body conduit. The tissue holding structure further may include a barb support member which supports the barb thereon and is axially movable within an internal lumen of the needle catheter. The needle catheter may be sized to deflect the barb radially inwardly during distal movement of the barb support member through the internal lumen of the needle catheter, and to subsequently allow the barb to return to an outwardly extending orientation after passage through the internal lumen. The barb support member may have an atraumatic distal tip portion. In a preferred embodiment, the barb support member extends distally from a flexible catheter.

The instrumentation may also include a connector for providing an anastomosis between the body conduit and a new length of body tubing comprising a first plurality of fingers for engaging an inner wall of the body conduit, a second plurality of fingers for engaging an outer wall of the body conduit, and a plurality of engagement members for securing the new length of body tubing to the connector. In one embodiment, the first plurality of fingers, the second plurality of fingers, and the engagement members are resiliently disposed radially outward.

Further instrumentation may be supplied to install the connector, including a connector support defining a longitudinal axis. The connector support may have a first retention structure to retain the first plurality of fingers towards parallelism with the longitudinal axis and a second retention structure to retain the second plurality of fingers towards parallelism with the longitudinal axis, such that the engagement members are disposed radially outwardly to facilitate attachment of the new length of tubing thereto. In an embodiment, the connector support and the instrumentation for cutting an opening in the body conduit may be one unit. Consequently, the connector support may define an interior lumen for receiving the tubular structure and tissue holding structure therethrough.

In a preferred embodiment, the first retention structure is an annular sleeve for retaining the first plurality of fingers distally towards parallelism with the longitudinal axis. The first retention structure retains the first plurality of fingers in a configuration having a dimension smaller than the opening in the body conduit.

The second retention structure may be a member having a projection received in a corresponding opening in each of the second plurality of fingers to retain the second plurality of fingers distally towards parallelism with the longitudinal axis. The second retention structure may also be an annular sleeve to retain the second plurality of fingers proximally towards parallelism with the longitudinal axis.

Instrumentation may also be provided to assist in the attachment of the new length of tubing to the connector. The new length of tubing may have a direction of natural fluid flow. For example, the saphenous vein normally has one-way valves to promote fluid flow in a single direction. In order to assist in the positioning of the new length of tubing, a sleeve sized for passage within the new length of tubing may be provided. The sleeve has an indicator to provide a visual indication of the direction of natural fluid flow. Additional instrumentation may include a pressure-application tool for facilitating the piercing of the new length of tubing by individual ones of the engagement members to secure the new length of tubing to the connector. The pressure-application tool may have a distal sleeve portion with an internal lumen sized such that individual ones of the engagement members may be received therein. The sleeve provides substantially uniform pressure to the new length of tubing about the engagement member to pierce the new length of tubing by the engagement member.

A method is also disclosed for performing an anastomosis between a body conduit and a new length of tubing which includes providing a tissue holding structure having a retention member to secure the body conduit to the tissue holding structure. Another step may be securing the retention member to the body conduit by at least partially inserting the tissue holding structure into the body conduit.

The method may also include providing a tubular structure having a sharpened distal portion. The body conduit and the sharpened distal portion of the tubular structure are approximated by relative movement of the tissue holding structure towards the tubular structure.

The method may also include cutting a section of the body conduit with the sharpened distal portion of the tubular body structure to provide an opening in the body conduit. The new length of tubing is attached to the body conduit adjacent the opening made by the cutting.

In a preferred embodiment, the method also includes providing a connector defining a central opening and having a first plurality of fingers for engaging an inner wall of the body conduit, a second plurality of fingers for engaging an outer wall of the body conduit, and a plurality of engagement members for securing a portion of the new length of body tubing to the connector. Attaching the new length of tubing to the body conduit adjacent the opening is performed by securing a portion of the new length of body tubing to the connector with the plurality of engagement members, engaging the inner wall of the body conduit with the first plurality of fingers, and engaging the outer wall of the body conduit with the second plurality of fingers.

In another embodiment, the method includes providing a connector support defining a longitudinal axis and having a first retention structure for retaining at least one of the plurality of fingers towards parallelism with the longitudinal axis, and prior to securing the portion of the new length of tubing to the connector, mounting the connector coaxially about the connector support and retaining one of the plurality of fingers with the retention structure.

Installation of the connector is performed by inserting the first plurality of fingers into the opening, releasing the retention structure to allow the first plurality of fingers to engage the inner wall of the body conduit, and releasing another retention structure to allow the second plurality of fingers to engage the outer wall of the body conduit.

Further features of the invention, its nature and various advantages will be more apparent from the accompanying drawings and the following detailed description of the preferred embodiments.

BRIEF DESCRIPTION OF THE DRAWINGS

FIG. 16 is an enlarged perspective view similar to a portion of FIG. 14, illustrating additional structure, in accordance with the invention.

FIG. 17 is a sectional view taken through line 17—17 of FIG. 16, in accordance with the invention.

DETAILED DESCRIPTION OF THE PREFERRED EMBODIMENTS

Although the invention has other possible uses, the invention will be fully understood from the following explanation of its use in providing a bypass around an obstruction in a patient's vascular system.

Figure 1:
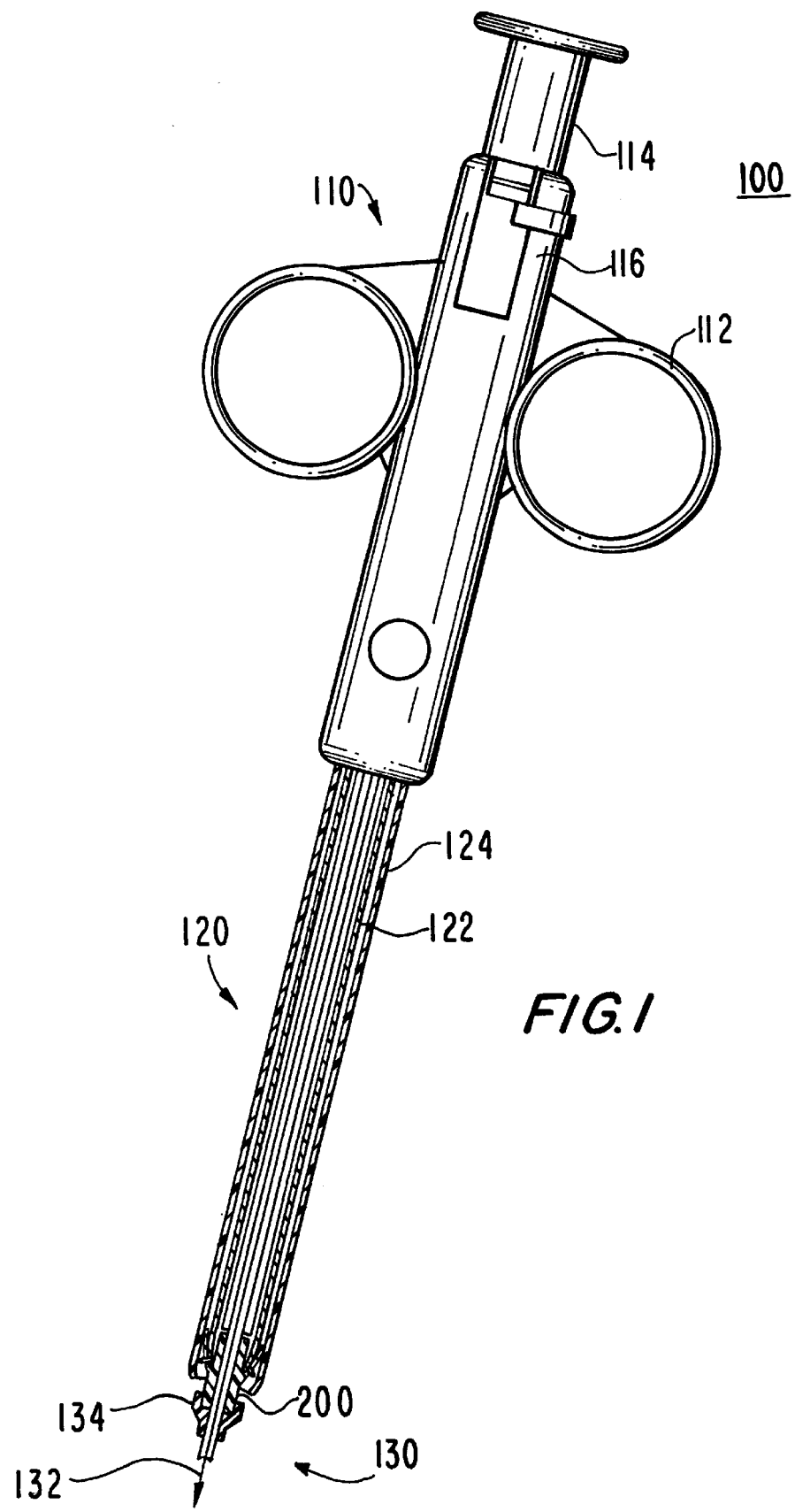
FIG. 1 is a simplified view in partial section of an apparatus in accordance with the invention.

An apparatus in accordance with the invention is illustrated in FIG. 1, and designated with the number 100. Apparatus 100 may include a proximal handle portion 110, an elongated medial portion 120, and a distal portion 130. According to a preferred embodiment, apparatus 100 has been illustrated as a single, integrated instrument. As will be described in greater detail herein, it is also contemplated that the various functions and/or the various components may be separated into a plurality of separate instruments.

The proximal handle portion 110 provides a suitable grip for the physician performing the process to be described in greater detail hereinbelow. Handle portion 110 may provide a plurality of actuation devices for operating the distal portion 130 of apparatus 100. Proximal handle portion 110 may be fabricated from surgical grade plastic or other similar material. Finger grips 112 and a plunger mechanism 114 may be provided to remotely operate certain distal components. In addition, a slide mechanism 116 with a lock mechanism may be provided to operate other distal components. The handle portion 110 disclosed herein is merely exemplary, and it is contemplated that alternative handle portions, such as, for example, a pistol grip or a lever mechanism, may be used to remotely operate the distal portion in accordance with the invention.

The medial portion 120 of apparatus 100 may consist of a series of concentric cylindrical members, and be fabricated with sufficient length to allow the physician to treat the patient's tissue by actuating the distal portion 130 of apparatus 100 from a distance away. According to the invention, the new length of tubing, such as the graft conduit 122 is mounted on the medial portion 120. The graft conduit may be a natural body conduit, such as a blood vessel or duct, or synthetic graft material. A delivery sheath 124 surrounds the graft conduit 122 during the process of attachment to an existing body conduit, such as the aorta.

The distal portion 130 of apparatus 100 performs a plurality of functions in the anastomosis. For example, the distal portion 130 may include a cutting mechanism 132 that provides an opening in the patient's existing body conduit. The distal portion 130 may also include a mechanism 134 for selectively deploying a connector apparatus 200, which attaches the graft conduit 122 to the existing body conduit.

When apparatus 100 is utilized by the physician to provide an anastomosis, the physician may perform the following sequence of steps. To prepare for the anastomosis, the connector 200 is attached to the distal end portion 130 of the apparatus. Subsequently, the graft conduit 122 is mounted to the medial portion 120 of the apparatus 100, and a distal end portion of the graft conduit 122 is attached to the connector 200. The cutting mechanism 132 provides an opening in a wall of the existing tubular body conduit. The connector deploying mechanism 134 then selectively deploys connector 200, which attaches the graft conduit 122 to the existing body conduit to complete the anastomosis. Each of the components and steps will be described in greater detail herein.

Figure 2:
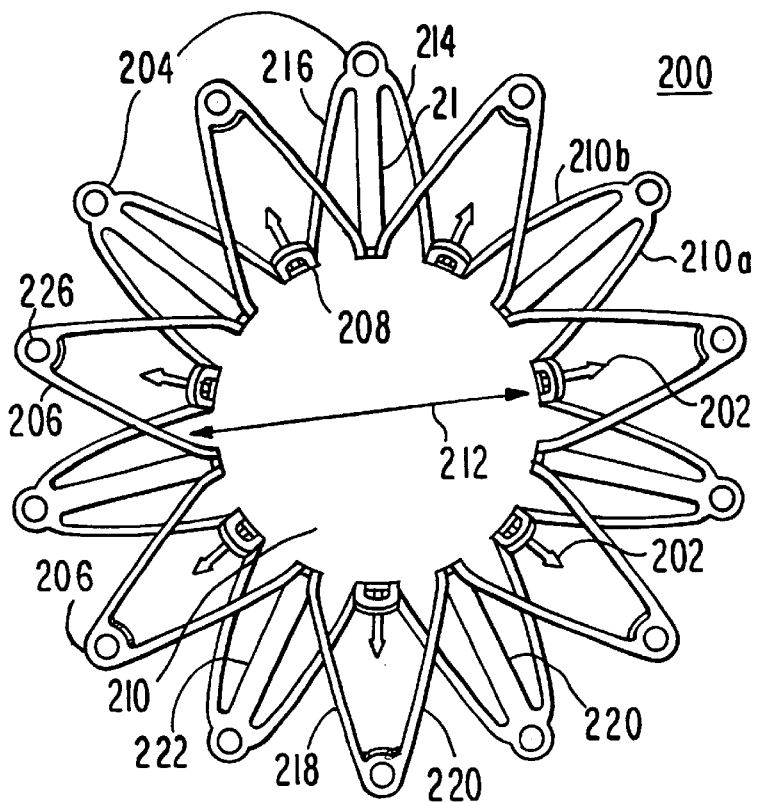
FIG. 2 is an elevational view of a connector apparatus, in accordance with the invention.
Figure 3:
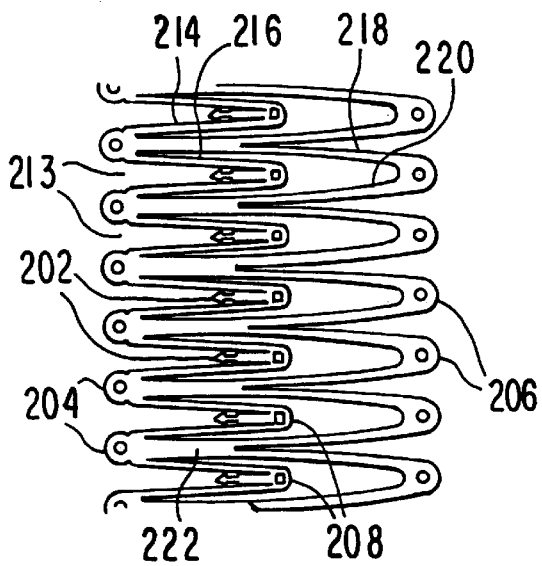
FIG. 3 is a simplified planar development, in reduced scale, of the connector apparatus of FIG. 2, in accordance with the invention.
Figure 4:
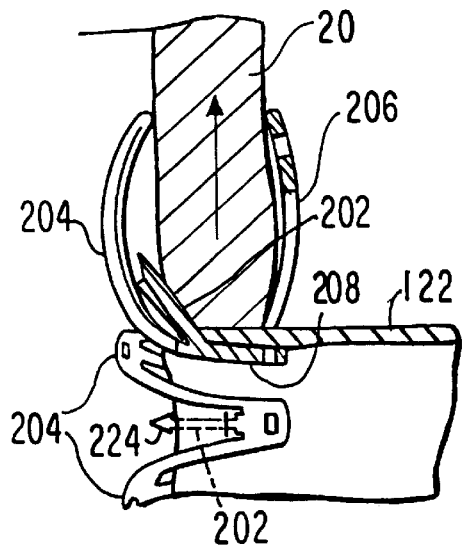
FIG. 4 is a simplified sectional view of the connector of FIG. 2 installed in a body conduit, in accordance with the invention.

FIGS. 2–4 illustrate a preferred embodiment of the connector apparatus 200. Additional features of the apparatus are disclosed in commonly-assigned, copending U.S. application Ser. No. 09/016,721 filed Jan. 30, 1998, and U.S. application Ser. No. 09/187,335 filed Nov. 6, 1998, both of which are incorporated in their entirety herein. Connector apparatus 200 may be preferably fabricated from a nickel-titanium alloy (nitinol). Connector apparatus 200 may include a plurality of fingers to engage the existing tubular body conduit and the new length of tubing in order to provide an anastomosis therebetween. A first plurality of fingers, such as graft attachment fingers 202, provide an attachment to the new length of tubing. A second plurality of fingers, internal fingers 204, engage the internal wall of the existing tubular body conduit. A third plurality of fingers, external fingers 206, engage the outer wall of the existing tubular body conduit. The pluralities of fingers are interconnected about a medial portion 208. Medial portion 208 defines a discontinuous, substantially circular enclosure 210 defining a nominal diameter 212. The flexible nature of the nitinol material and the discontinuity of medial portion 208 permits connector apparatus 200 to expand and contract with respect to diameter 212.

According to a preferred embodiment, connector apparatus 200 may be manufactured from a substantially cylindrical tube (not shown) of nitinol material. A laser is preferably used to cut a particular configuration into the tube. FIG. 3 illustrates a planar development of the configuration of connector apparatus 200, e.g., were the clinical tube to be cut and flattened to a two-dimensional configuration. As can be seen in FIG. 3, the pluralities of fingers have been formed from the cutting process, thus forming a plurality of open spaces 213 between fingers. Each of the pluralities of fingers is interconnected adjacent the medial portion 208. More particularly, each internal finger 204 has outer struts 214 and 216 connected to an adjacent medial portion 208. Each external finger 206 has outer struts 218 and 220 connected to center strut 222 of internal finger 204 in a region adjacent medial portion 208. Once the nitinol tube has been cut to form the various fingers described hereinabove, the fingers are deflected radially outwardly and may be heat treated to form the configuration shown in FIGS. 2 and 4.

As illustrated in FIG. 4, connector apparatus 200 provides a secure attachment between a new length of tubing 122 and the existing tubular body conduit, such as the aorta 20. Preferably, this connection is located between the end portion of the graft conduit 122 and an aperture in the wall of the existing tubular body conduit 20. The internal fingers 204 engage the internal wall of the existing tubular body conduit 20, and assist in positioning the connector apparatus 200 and the new length of tubing 122 relative to the existing tubular body conduit 20. The internal fingers 204 also assist in the mechanical retention of the connector apparatus 220 to the existing tubular body conduit 20. The external fingers 206 engage the external wall of the existing tubular body conduit 20, and assist in positioning the connector apparatus 200 and the new length of tubing 122 relative to the existing tubular body conduit 20. The internal fingers 204 also assist in the mechanical retention of the connector apparatus 200 to the existing tubular body conduit 20. The medial portion 208 allows the connector to expand radially outwardly (such as in the direction shown by the arrow in FIG. 4). This expansion compresses the wall of the new length of tubing 122 against the wall of the existing tubular body conduit 20 to produce a hemodynamic seal. The graft attachment members 202 provide a means for attaching the new length of tubing 122 to the connector apparatus 200. Preferably, graft attachment members 202 have a sharpened end portion to pierce the new length of tubing 122 and a barbed configuration 224 to secure the new length of tubing once attached.

Figure 5:
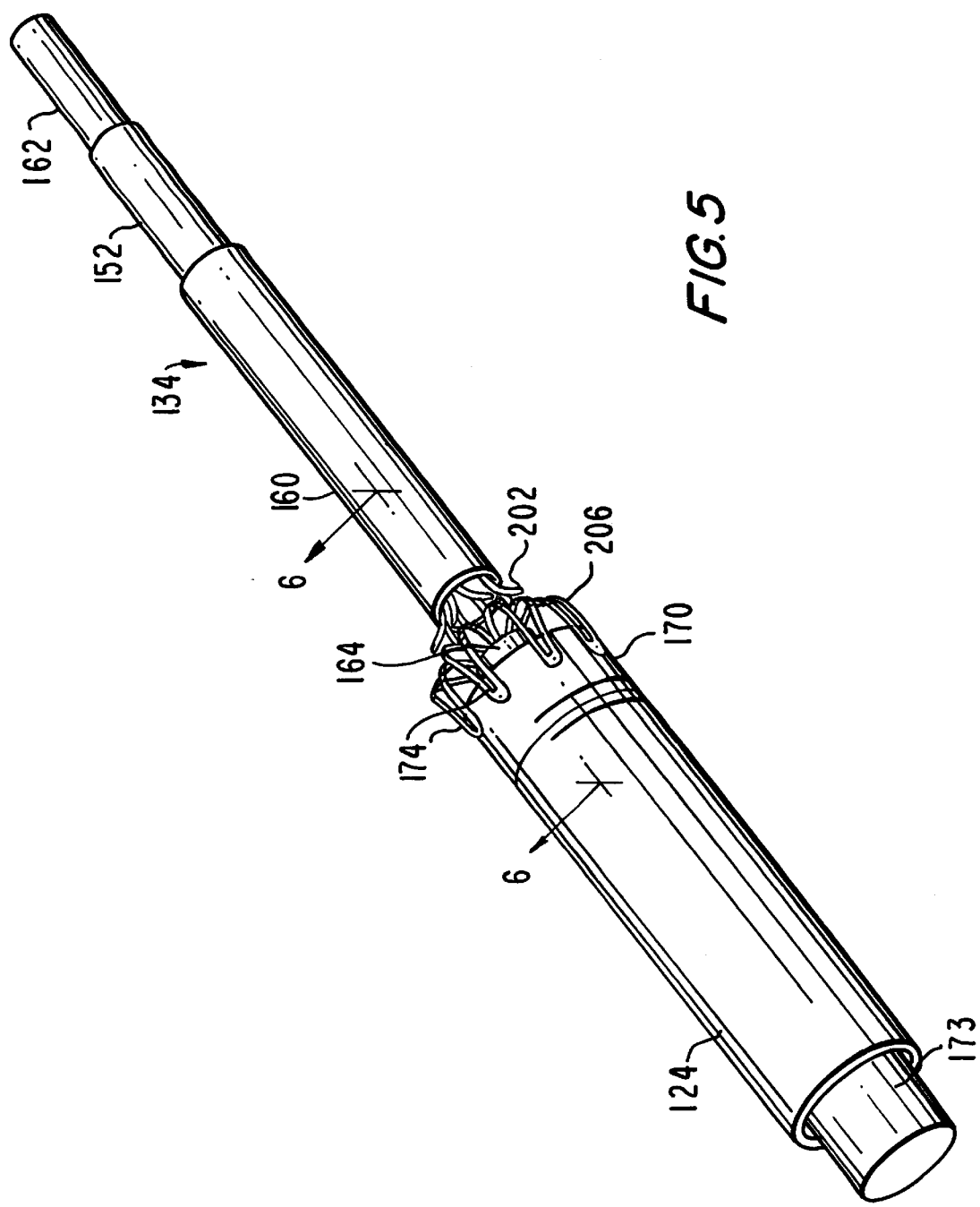
FIG. 5 is a perspective view of the connector of FIG. 2, mounted within a portion of the apparatus of FIG. 1, and additional structure, in accordance with the invention.
Figure 6:
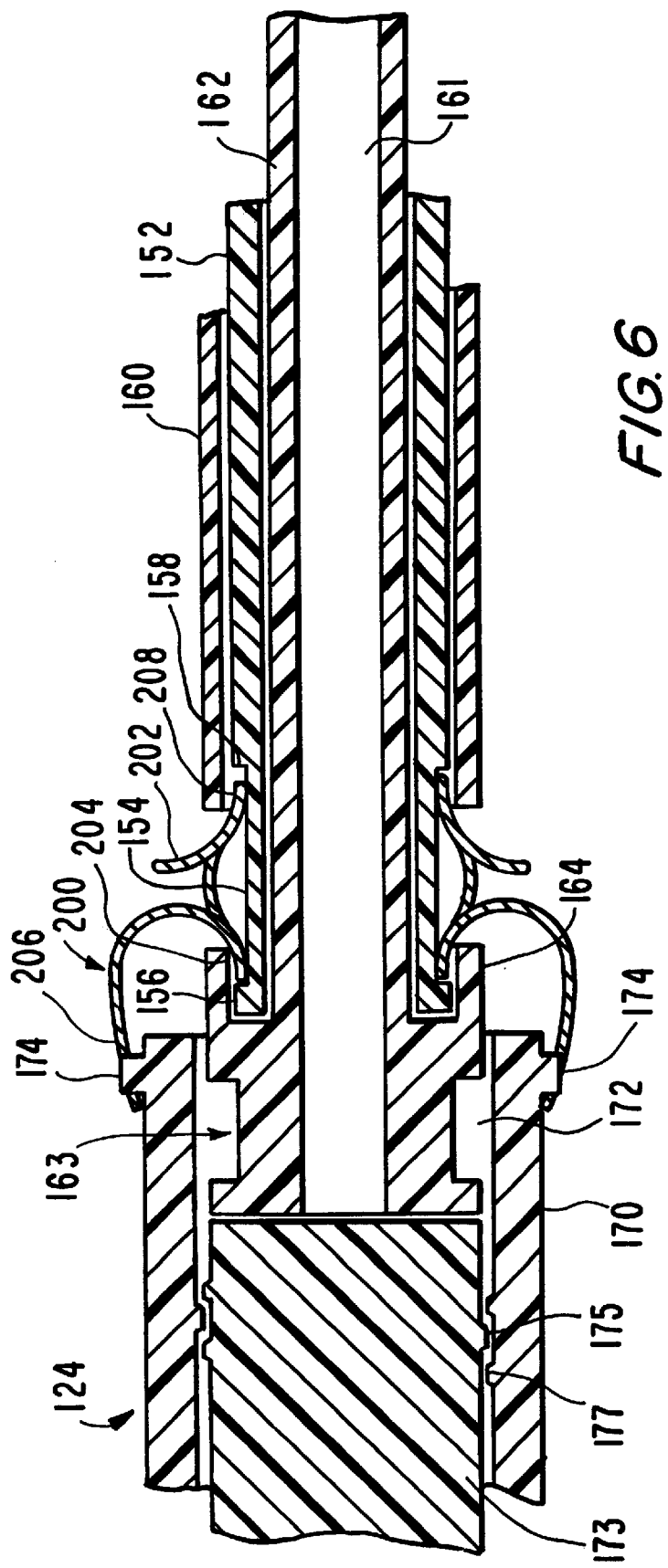
FIG. 6 is a sectional view of the connector and apparatus illustrated in FIG. 5, in accordance with the invention.

An early step in the installation of the connector apparatus 200 in a patient is the mounting of the connector apparatus 200 to a connector support structure 134 in order to facilitate attachment of a graft conduit to the connector (FIGS. 5 and 6). More particularly, connector 200 is positioned about connector support member 152. The distal end portion of connector support member 152 is provided with an annular recess 154, having a distal shoulder portion 156 and a proximal shoulder portion 158. Connector 200 is positioned in the annular recess 154 such that internal fingers 204 are adjacent distal shoulder portion 156 and medial portions 208 are adjacent proximal shoulder portion 158.

A first member, such as outer retention member 160, surrounds medial portions 208 and retains them in position. A second member, such as inner retention member 162, is positioned coaxially within a lumen of connector support member 152. A distal end portion 163 of inner retention member 162 may be provided with an annular sleeve portion 164, which surrounds the internal fingers 204 and retains them in position with respect to the annular recess 154 and shoulder portion 156. Inner retention member 162 is configured for longitudinal movement with respect to the connector support member 152. In a preferred embodiment, inner retention member may be actuated by slide mechanism 116 located on the proximal handle portion (see, FIG. 1).

During this stage of the installation, delivery sheath 124 may be positioned adjacent the distal portion of the connector support structure 134. The proximal end portion of delivery sheath 124 may be provided with a connector retention fixture portion 170. Retention fixture 170 may have an internal lumen, or cylindrical bore 172, to coaxially surround the distal end portion 163 of inner retention member 162. A positioning member 173 may be located with bore 172 of delivery sheath 124. An outer threaded portion 175 is provided on a distal portion of positioning member 173 and cooperates with an inner threaded portion 177 provided on sheath 124. The threaded portions 175 and 177 may be relatively rotated in order to secure the positioning member 173 with respect to the delivery sheath 124. The positioning member 173 is provided with a proximal surface which abuts the distal end portion 163 of inner retention member 162 and thereby stabilizes the fixture portion 170 of the delivery sheath 124 against relative longitudinal movement with respect to the inner retention member 162 during this stage of the installation.

The outer periphery of retention fixture 170 is provided with a plurality of mounting tabs 174. (The mounting tabs 174 and 174' are illustrated in greater detail in FIGS. 10 and 10(a), below.) Each of the external fingers 206 is deflected distally and towards parallelism with the longitudinal axis towards mounting tabs 174. Each external finger may be attached to a mounting tab 174. It is also contemplated that positioning member 173 and fixture portion 170 may be substituted with a single component (not shown) that abuts the distal portion 163 of inner retention member 162 and provides mounting tabs 174 for external fingers 206.

As a consequence of mounting connector 200 as described above, graft attachment members 202 are oriented radially outward, and provide attachment points for the new length of tubing, as will be described in greater detail hereinbelow.

Figure 7:
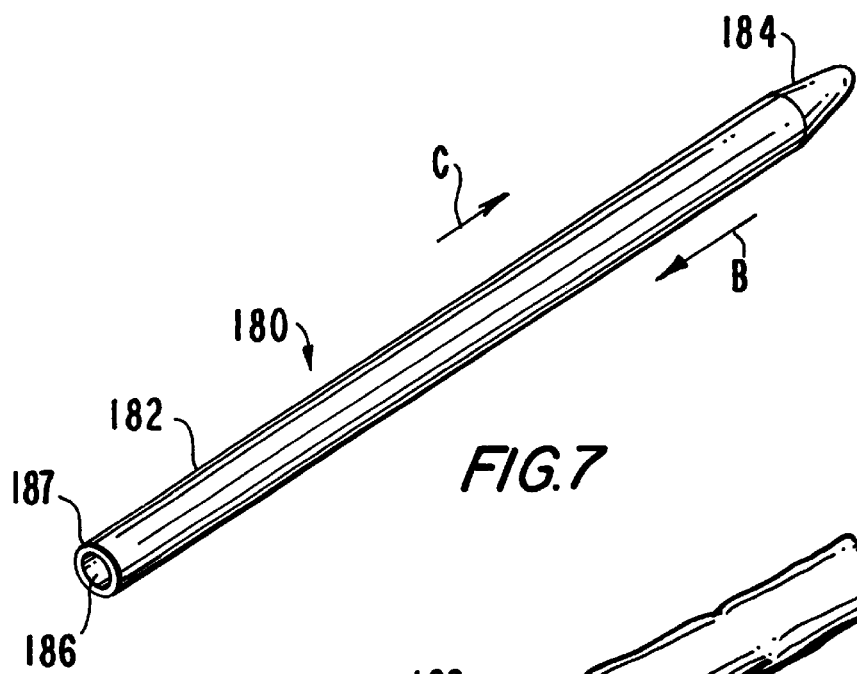
FIG. 7 is a perspective view of additional structure for use with the FIG. 5 apparatus, in accordance with the invention.

The graft transfer sheath 180, illustrated in FIG. 7, assists in the mounting of the new length of tubing 122 onto the apparatus 100, and more particularly, the connector support mechanism 134, without compromising the delicate intima of the new length of tubing. The graft transfer sheath 180 is preferably fabricated from a low friction, biocompatible polymer such as, e.g., polyethylene or polytetrafluoroetylene, or similar material. The sheath 180 may alternatively be made of metal, such as, e.g., stainless steel. The sheath 180 may have an elongated body portion 182, a tapered end proximal portion 184, and an internal lumen 186. The tapered tip portion 184, having an atraumatic tip, allows the new length of tubing to be loaded over the sheath 180, in the direction indicated by arrow B.

The graft transfer sheath may also assist the physician in properly orienting the new length of tubing with respect to the intended fluid flow direction when the tubing is in place. For example, if the new length of tubing is a vein, it may have internal valves to restrict the direction of flow. When the vein is utilized as arterial blood source, the graft may be reversed in order to allow flow in the opposite direction. As illustrated in FIG. 7, the graft transfer sheath 180 provides a visual indication to the physician of the desired flow direction, i.e., from the distal opening 187 to the tapered tip portion 184, as indicated by arrow C.

The graft transfer sheath 180 also assists the physician by serving as a sizing instrument. The outer diameter of the body portion 182 is selected to accommodate a graft having a diameter which is compatible with the connector 200. For example, a graft that is too narrow will not be able to receive the sheath 180 therethrough. In a preferred embodiment, body portion 182 of sheath has a diameter of about 3 mm. The diameter of body portion 182 may be fabricated with a different diameter, and corresponding connector size, depending upon the specific clinical indication of the graft size and desired anastomosis size.

Figure 8:
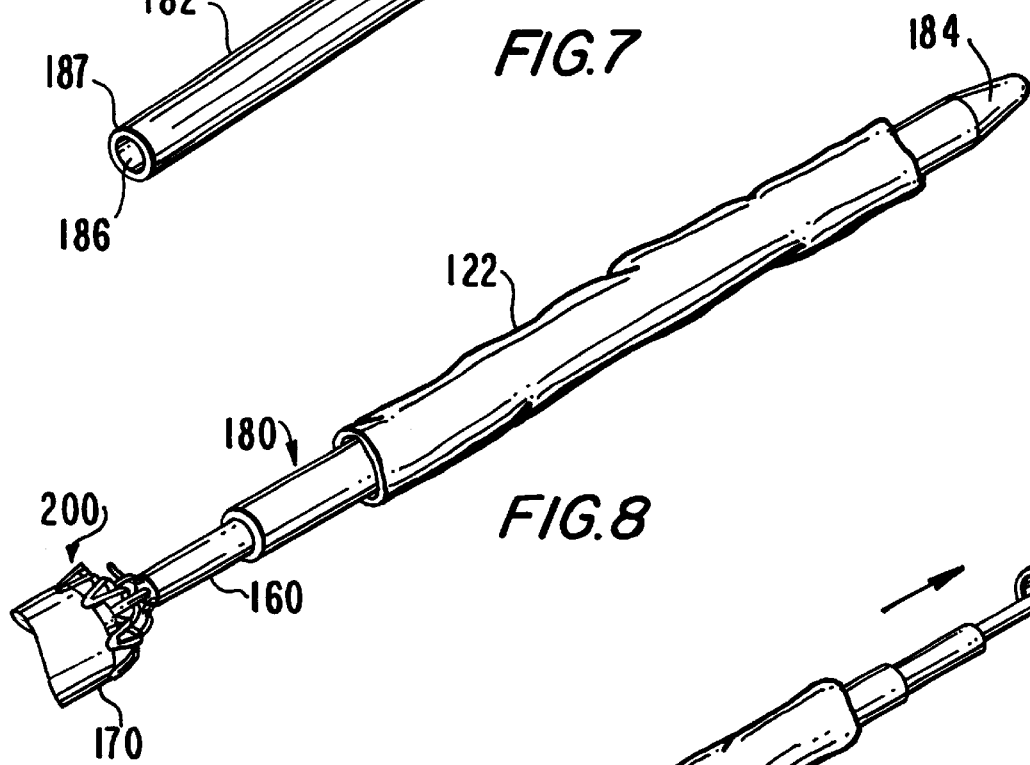
FIG. 8 is a perspective view of the connector and apparatus of FIGS. 5–6, illustrated in combination with the structure of FIG. 7, in accordance with the invention.
Figure 9:
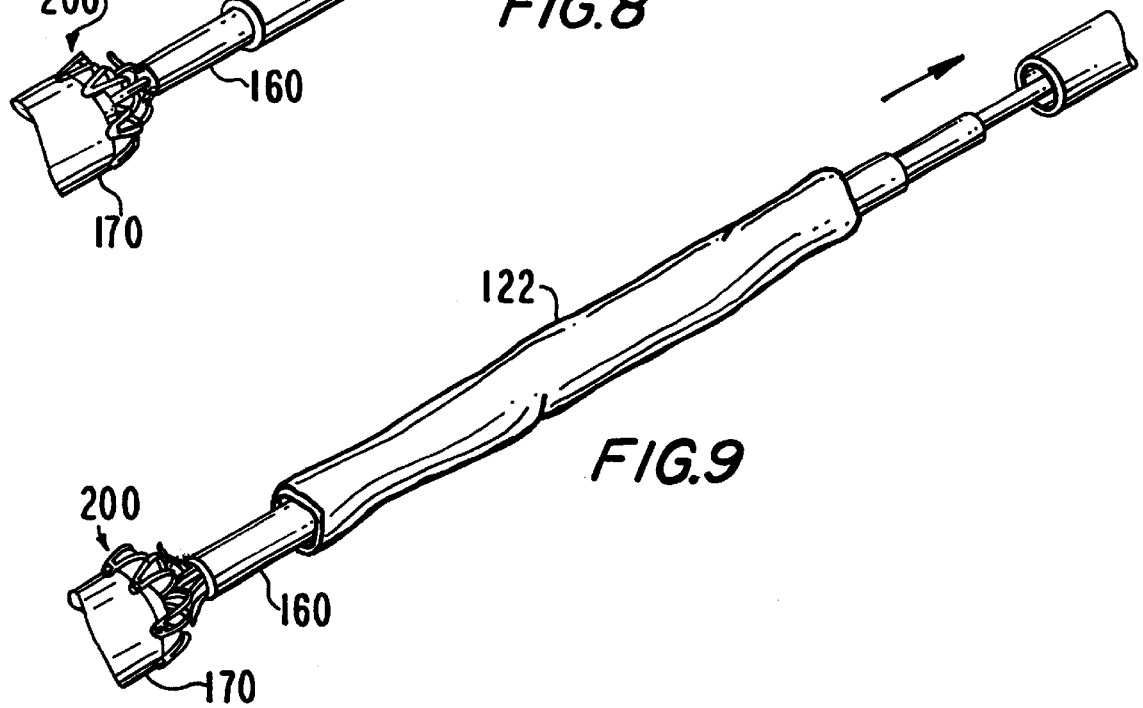
FIG. 9 is a perspective view similar to FIG. 8, illustrating a later stage in the use of the apparatus of FIG. 8, in accordance with the invention.
Figure 10:
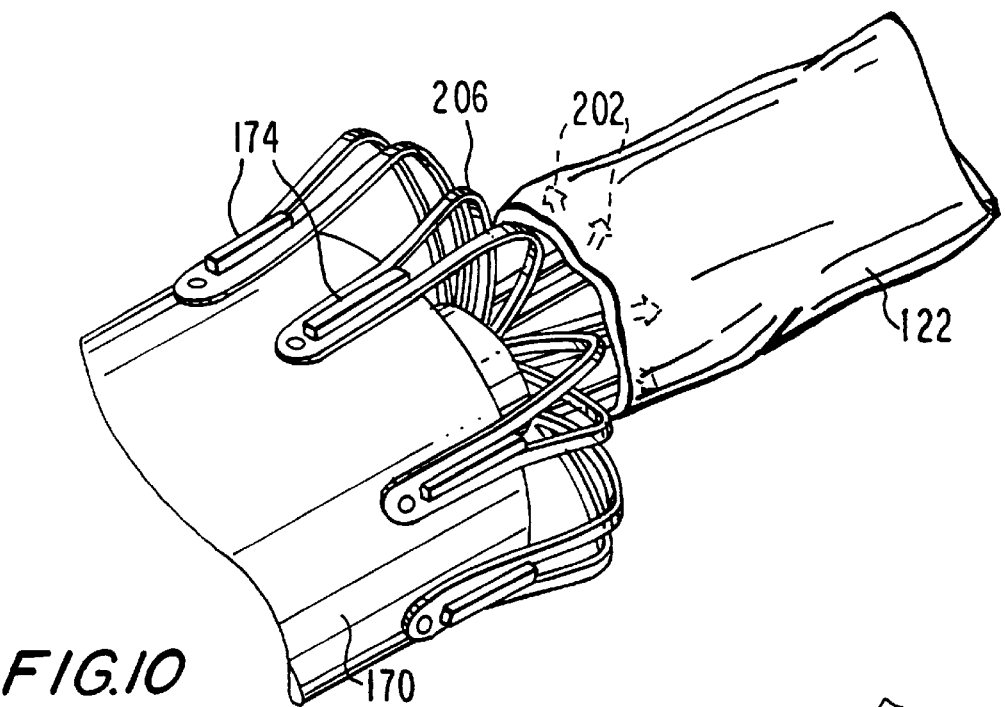
FIG. 10 is an enlarged perspective view similar to FIG. 9, illustrating a still later stage in the use of the apparatus of FIG. 9, in accordance with the invention.
Figure 10A:
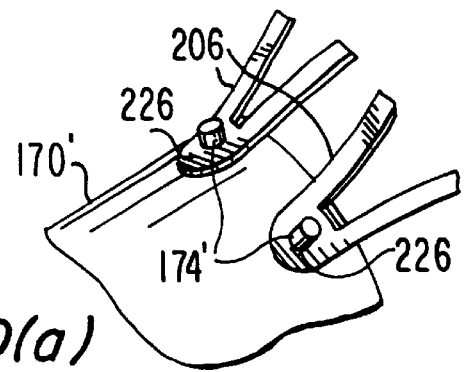
FIG. 10(a) is an alternative embodiment of the structure illustrated in FIG. 10.

Once the graft 122 is harvested, it is positioned over the sheath 180, as described above. As illustrated in FIG. 8, the sheath 180 and graft 122 are passed coaxially over the connector support member 160 towards the connector 200, in the direction as indicated by the arrow. Subsequently, the graft 122 is retained in position (e.g., with an atraumatic grasping instrument), and the sheath 180 is removed from the connector support member 160, as indicated by the arrow in FIG. 9. The graft 122 is positioned with respect to the connector 200 such that an end portion of the graft surrounds the outwardly facing graft attachment members 202, as illustrated in dashed line (FIG. 10). An alternative embodiment of the fixture is illustrated in FIG. 10(a), and designated by reference number 170', and utilizes a plurality of circular mounting tabs 174', which may be received in apertures 226 provided on outer retention fingers 206.

Figure 11:
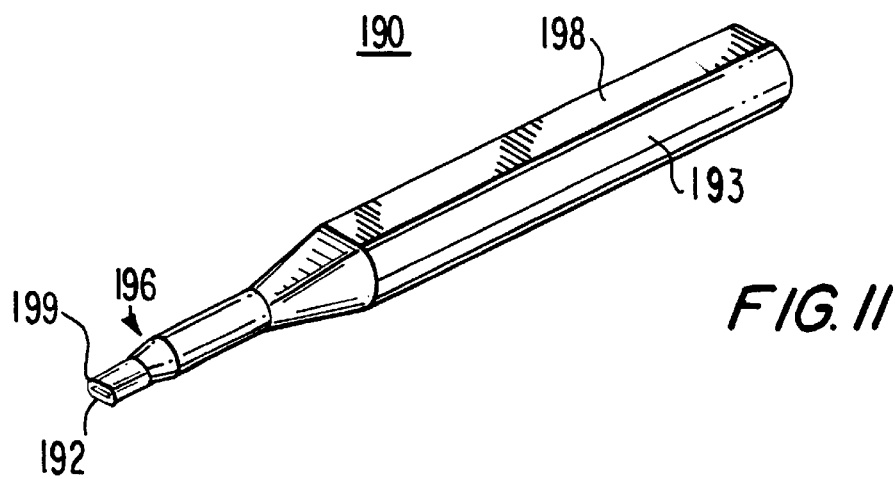
FIG. 11 is a perspective view of additional structure for use with the FIG. 10 apparatus, in accordance with the invention.

FIG. 11 illustrates apparatus useful in piercing the graft 122 with the graft attachment members 202. More particularly, vein piercing tool 190 is provided with hollow tubular tip 192 that allows the physician to pierce the graft 122 at the desired location. Vein piercing tool 190 preferably has a proximal handle portion 193 and a distal portion 196 with the hollow tubular tip 192. The tool 190 may be provided with flattened portion 198 which corresponds to the major axis 199 of the tip 192. The flattened portion 198 provides a tactile indication to the physician to assist in determining the location of the major axis 199.

Figure 12:
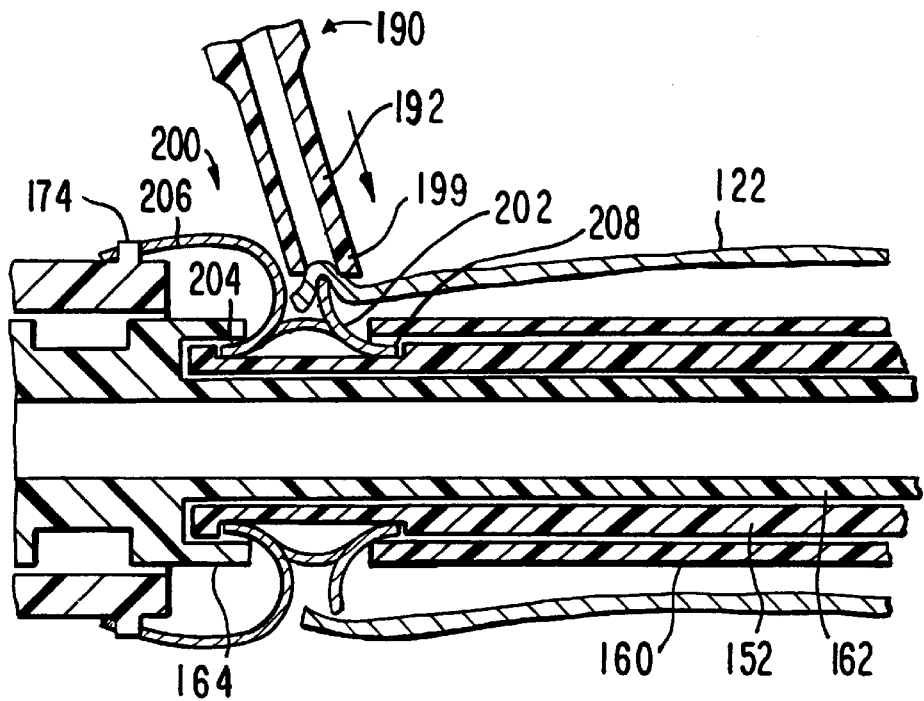
FIG. 12 is a sectional view of the FIG. 10 apparatus, illustrating a stage in the use of the FIG. 11 apparatus, in accordance with the invention.
Figure 13:
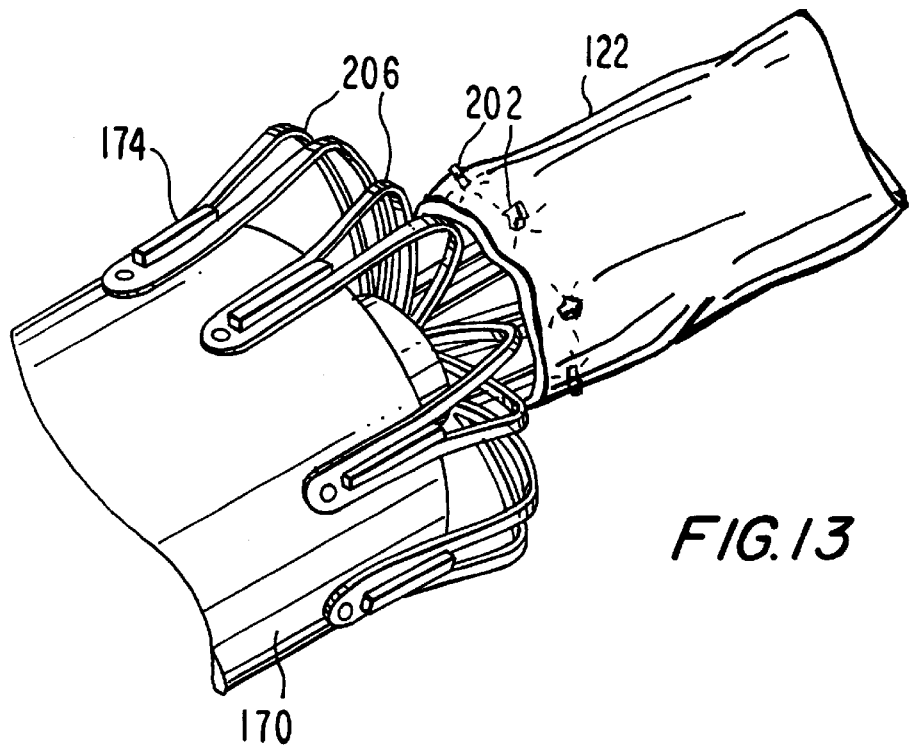
FIG. 13 is an enlarged perspective view of the FIG. 12 apparatus, in accordance with the invention.

FIG. 12 illustrates the manner in which the vein piercing tool 190 may be used to assist the piercing of the graft 122 with the graft attachment members 202. After the graft is oriented about the connector as described above with respect to FIG. 10, the vein piercing tool 190 is brought into approximation with the graft 122. More particularly, the hollow tubular tip 192 contacts the graft 122 about the barbed tip of the graft attachment member 202. The flattened portion 198 (not shown in the FIG.) allows the surgeon to locate and position the major axis 199 of the tip 192 which contacts the graft tissue first. Pressing down on the tip 192 (as indicated by the arrow) applies substantially uniform pressure to the graft 122 about the graft attachment member 202 to provide a neat piercing without tearing the graft tissue. The vein piercing tool 190 is subsequently used with each graft attachment member 202, in order to provide the attached configuration as illustrated in FIG. 13. The physician may then test the attachment of the graft 122 to the graft attachment members 202, for example, by applying a gentle proximal force to the graft 122 adjacent the attachment locations.

Figure 14:
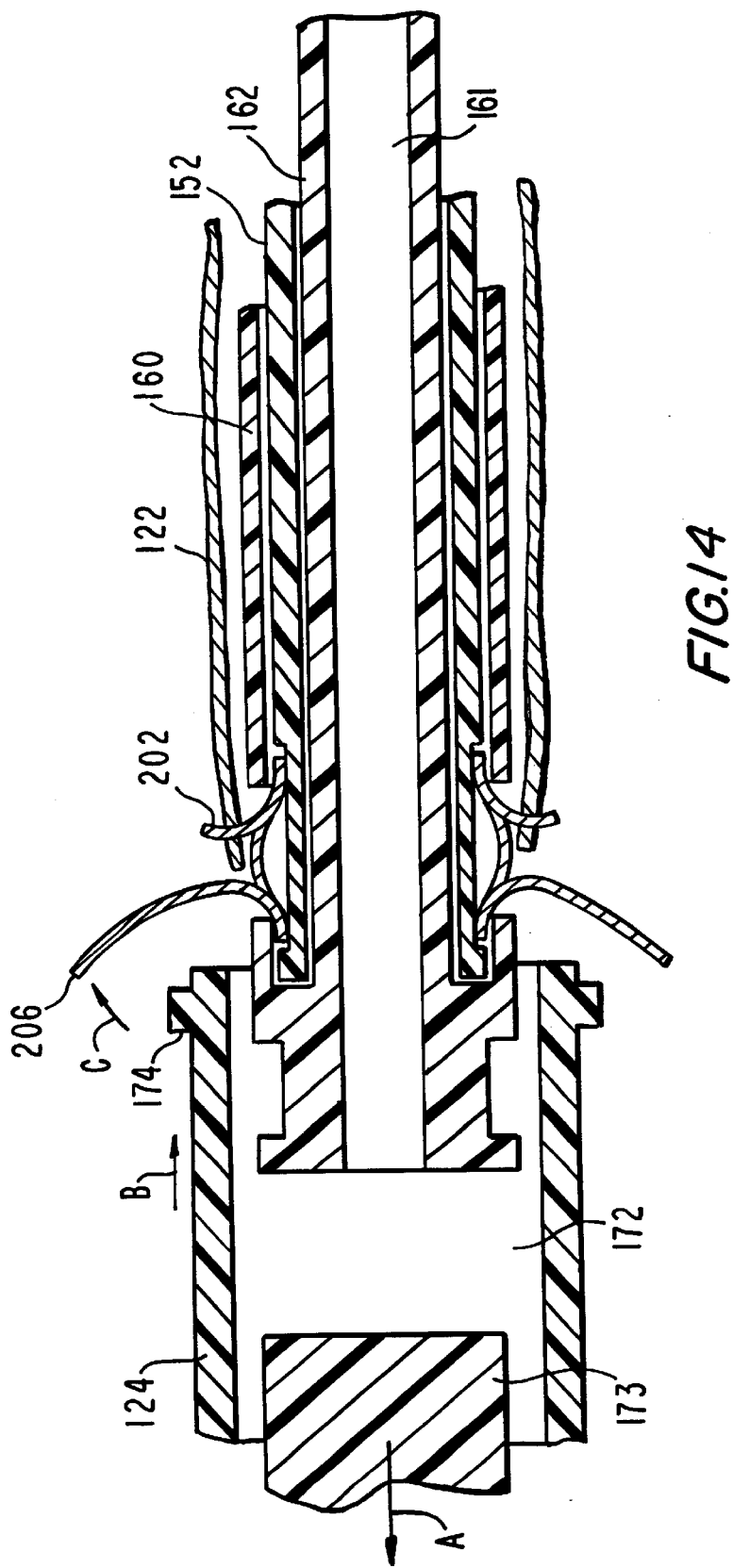
FIG. 14 is a sectional view similar to FIG. 6 illustrating a later stage in the use of the apparatus, in accordance with the invention.

A later stage in the use of apparatus 100 is illustrated in FIGS. 14 and 15. During the graft attachment steps (FIGS. 10–13), the external fingers 206 are deflected distally to allow access to the graft attachment fingers 202, by attachment to retention fixture 170. After graft attachment, the external fingers 206 are released from attachment to retention fixture 170, as illustrated in FIG. 14. According to one embodiment, this may be accomplished by advancing the delivery sheath 124 proximally over the connector apparatus 200. Initially, delivery sheath 124 and positioning member 173 may be secured against relative longitudinal movement by cooperating threaded portions 175 and 177 (see, FIG. 6).

As illustrated in FIG. 14, positioning member 173 may be removed from within bore 172 by unscrewing the threaded portions 175/177 and withdrawing the positioning member 173 distally (as indicated by arrow A). Consequently, delivery sheath 124 is relatively longitudinally moveable with respect to connector 200. Delivery sheath 124 may be advaced proxmally (as indicated by arrow B), which allows external fingers 206 to be released from mounting tabs 174. External fingers 206 expanded radially outward upon relese from mounting tabs 174 (as indicated by arrow C).

In the alternative embodiment illustrated in FIG. 10(a), each external finger 206 is removed from the associated tab 174', and the retention fixture 170' may be removed from the device.

Figure 15A:
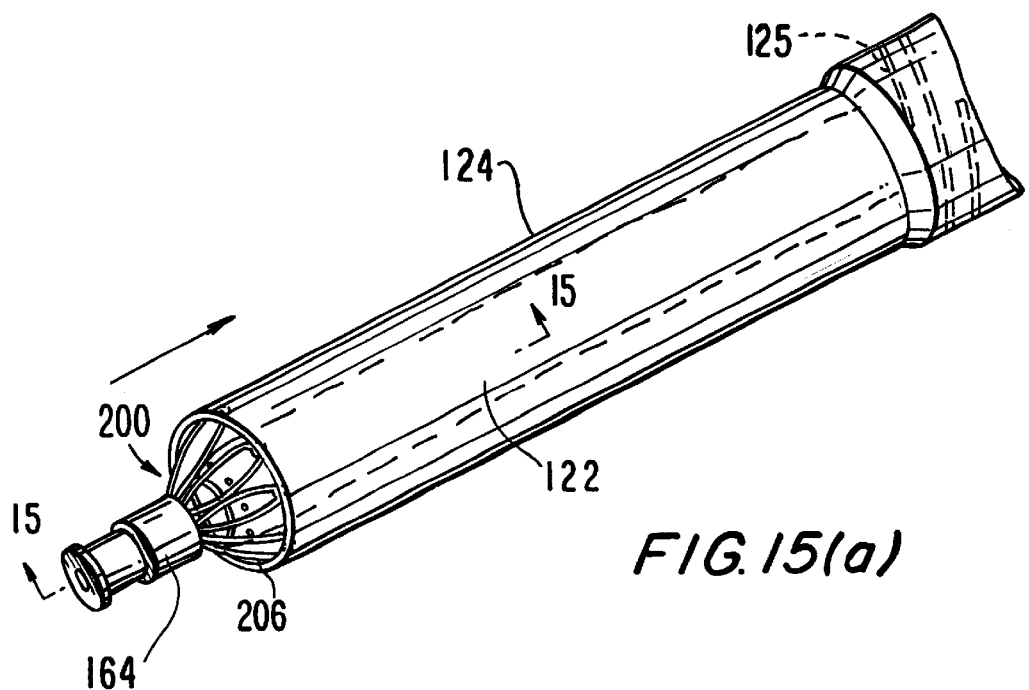
FIG. 15(a) is a perspective view illustrating additional structure, in accordance with the invention.
Figure 15B:
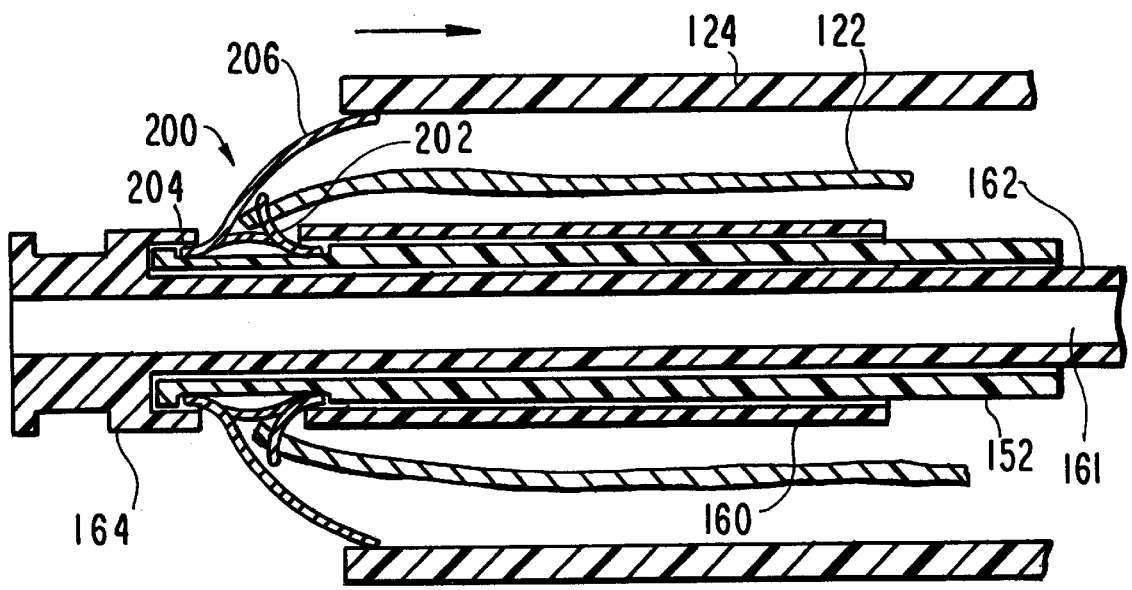
FIG. 15(b) is a sectional view taken through line 15—15 of FIG. 15(a), in accordance with the invention.

FIG. 15(a) illustrates a subsequent step wherein the delivery sheath 124 is advanced further proximally to a surrounding configuration over the connector 200 and the graft conduit 122. Preferably, the sheath 124 is mounted from the distal end towards the proximal end of the device (as indicated by the arrow). Delivery sheath 124 is provided with mounting threads 125 (illustrated in dashed line) which may be secured to the handle 110. The length of the delivery sheath 124 is selected such that the external fingers 206 are deflected and secured proximally towards parallelism with the longitudinal axis, as shown in FIGS. 15(a) and 15(b).

The nosecone 310 and cutting mechanism 132 may be attached to the apparatus 100 as illustrated in FIGS. 16 and 17. Additional features and methods for creating an aperture at the anastomosis site are disclosed in commonly-assigned Berg et al. U.S. Pat. No. 6,416,527, which is incorporated by reference in its entirety herein. The nosecone 310 is placed over the distal portion 163 of the inner retention member 162. The nosecone 310 may have a body portion 312 which is movable with the inner retention member 162. A plurality of leaves 314 extend proximally from the body portion 312. Each leaf 314 is positioned between struts 218 and 220 of each external finger 206, and covers a graft attachment member 202. As will be explained in greater detail below, each leaf 314 is resiliently biased radially inwardly. Leaves 314 cover the graft attachment members 202 during insertion into the body conduit, and prevent the sharpened tip portions of members 202 from inadvertently tearing or snagging on tissue.

The cutting mechanism 132 is mounted distally of the nosecone 310, and may be positioned within internal lumen 161 of inner retention member 162. Cutting mechanism 132 includes a tissue holding structure, such as stylet 322, which pierces and retains tissue, and a tubular structure, such as coring tip 324, which cuts a plug of tissue retained by the stylet 322, thus providing an opening for the anastomosis. As will be described in greater detail below, the tissue holding structure 322 includes a distal piercing portion, such as angled needle tip 326, similar in construction to a tip used, e.g., in a hypodermic needle. The tissue holding structure 322 includes retention members, such as proximally extending barbs 328. In the embodiment illustrated in FIGS. 16–17, the distal piercing portion 326 and the proximally extending barbs 328 are provided on a single, integrated unit, such as stylet 322. It is contemplated that the distal piercing portion and the proximally extending barbs are provided on separate parts, as will be described below. The stylet 322 is mounted on a support shaft 330 for relative longitudinal motion with respect to coring tip 324. Briefly, the stylet 322 is constructed to pierce the tissue with the needle tip 326 from the entrance side of the tissue to the exit side. The stylet 322 is retracted proximally to allow the barbs 328 to engage the exit side of the tissue, such that the tissue that has just been pierced is now engaged between the barbs 328 and the coring tip 324. The coring tip is then used to core out a small cylindrical section of tissue, which is retained by the barbs 328 of the stylet 322. According to one embodiment, the coring tip 324 is provided with an edge that cores the tissue by rotation about the longitudinal axis. According to another embodiment, the coring tip 324 has an edge which cores the tissue by longitudinal advancement through the tissue. It is also contemplated that coring may be performed by a combination of rotation and longitudinal advancement. These procedures provide a smooth, uniform circular hole in the tissue.

Figure 18:
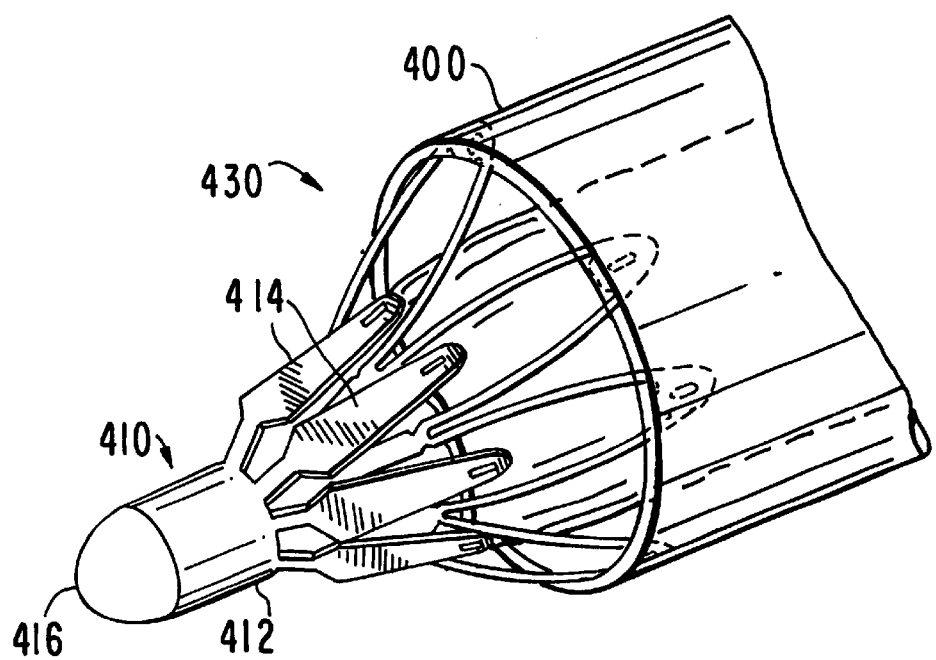
FIG. 18 is a perspective view of an alternative embodiment of the apparatus illustrated in FIGS. 16–17, in accordance with the invention.
Figure 19:
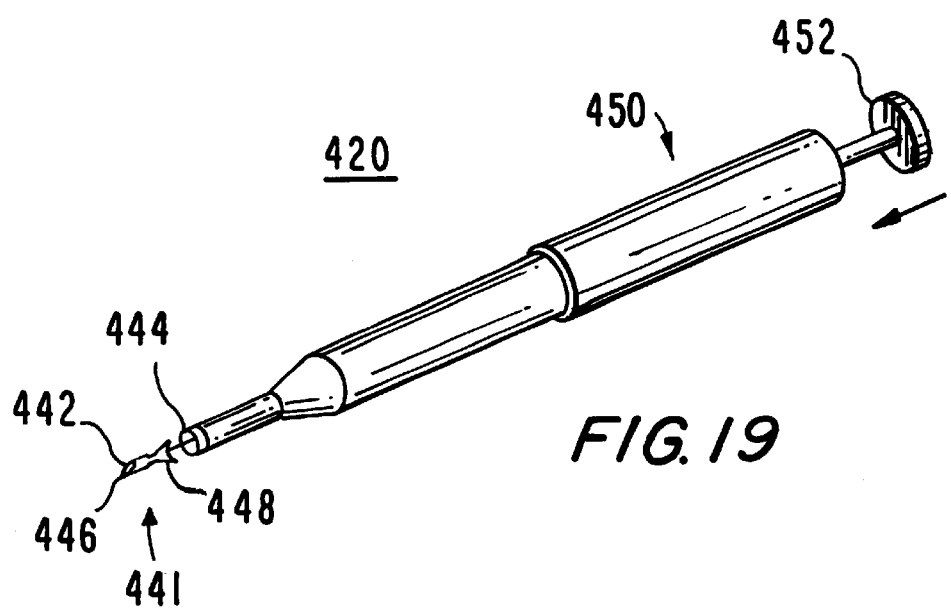
FIG. 19 is a perspective view of additional structure useful in connection with the alternative embodiment illustrated in FIG. 18, in accordance with the invention.

An alternative embodiment of the nosecone and cutting mechanism is illustrated in FIGS. 18 and 19. Under certain surgical conditions, it may be useful or preferable to provide one instrument for deploying the connector and graft, and a separate instrument for providing an aperture in the body conduit to which the connector and graft are to be attached. FIG. 18 illustrates an alterative embodiment of the distal end portion 430 of an apparatus 400 for deploying the connector and graft. Apparatus 400 is substantially identical to apparatus 100, as illustrated in FIGS. 1 and 16 and as described hereinabove. For example, apparatus 400 may have a plurality of leaves 414 extending proximally from a body portion 412 that are substantially identical to elements 312 and 314 shown in FIG. 1. Several of the substantial differences between apparatus 400 and apparatus 100 are noted herein. For example, the cutting mechanism 132 depicted in FIGS. 16 and 17 has been eliminated from apparatus 400. A modified nosecone 410 is provided which has an atraumatic tip portion 416, which may be hemispherical or conical.

The function of cutting an aperture in the body conduit is provided by a cutting apparatus 420 (FIG. 19). The distal portion 441 is substantially identical to the cutting mechanism 132, described with respect to FIGS. 16 and 17. More particularly, the distal portion 441 includes a stylet 442 which pierces and retains the tissue, and a coring tip 444 which cuts the opening for the anastomosis. The stylet 442 has needle tip 446 for piercing the tissue and barbs 448 on the proximal portion thereof. The barbs 448 and the coring tip 444 retain the tissue therebetween.

The proximal handle portion 450 includes a plunger-type mechanism 452 to actuate the distal portion 441. The preferred mechanism is an internal spring bias which urges the stylet 442 proximally. The physician depresses the plunger-type mechanism 452 (as indicated by the arrow) which advances the stylet 442 distally against the spring bias. After releasing the mechanism 452, the spring retracts the stylet 442 proximally towards the coring tip 444. This configuration secures the tissue being cut between the barbs 448 and the coring tip 444. The physician may rotate the proximal handle portion 450 and the coring tip 444 therewith about the longitudinal axis and/or advance the apparatus 420 to core out a small cylindrical section of tissue.

Figure 20:
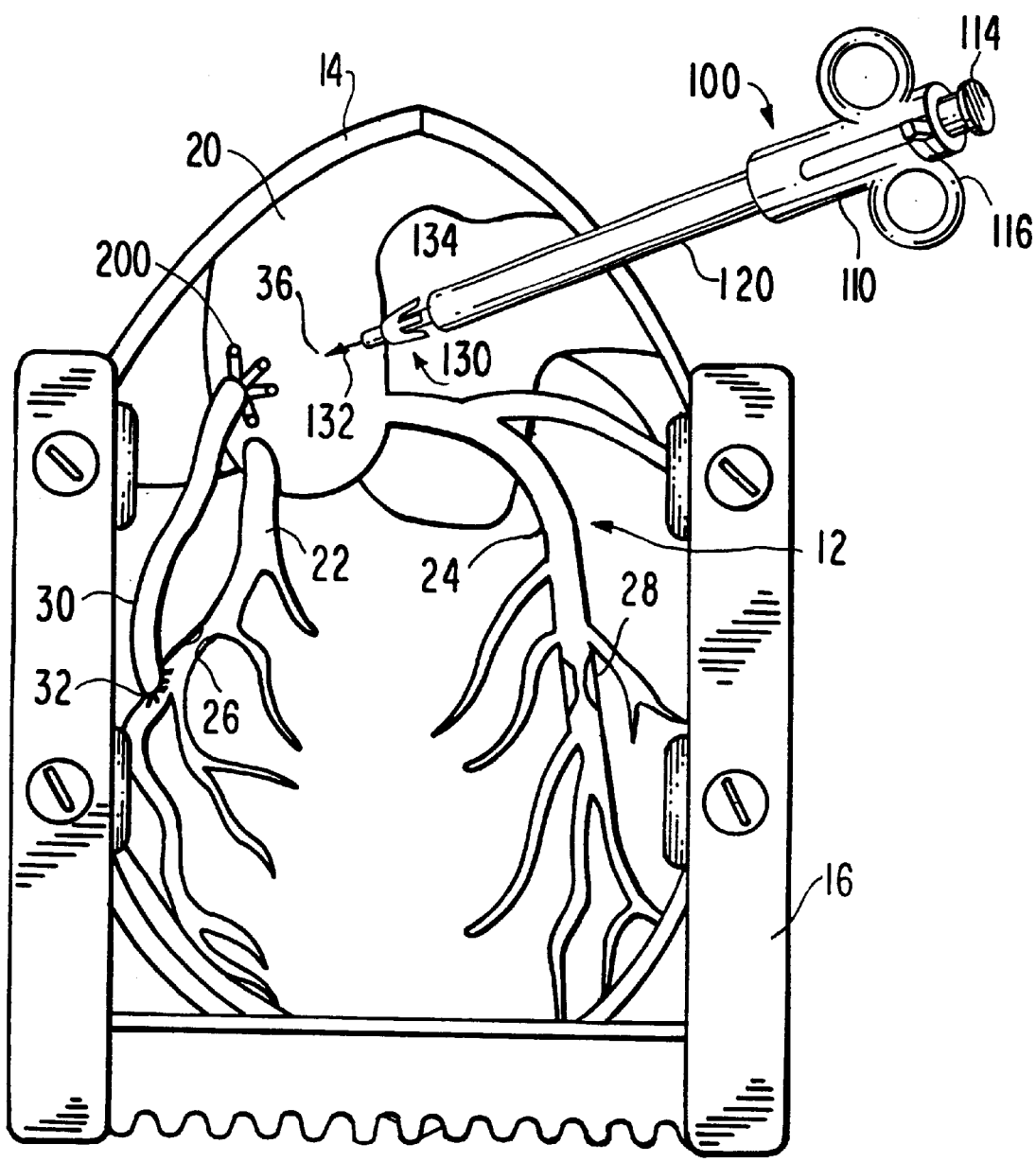
FIG. 20 is a simplified view of an early stage in the use of the apparatus of FIG. 1, in accordance with the invention.

FIG. 20 illustrates an early stage in the use of apparatus 100 in accordance with the invention. The physician provides surgical access to the operative site. Surgical access provides improved visibilty to the physician during the procedure. It may also allow management of bleeding by the introduction of equipment to remove blood from the operative cavity as well the introduction of eqipment to irrigate the region. This approach also allows for the removal of inconsequential tissue such as fascia and fat from the anastomosis sites.

Accordingly, the region above the operative site on the skin surface of the patient is located. As illustrated in FIG. 20, the location of heart 12 in the chest of the patient is found. An incision 14 is made in the chest. Although reference is made to a single incision, it is contemplated that several incisions and access points may be made. A retractor clamp 16 may be applied to the incision to hold it in an open position. In a further alternative embodiment, the retractor clamp may be configured to partially deflect the ribs apart. In an alternative embodiment, a trocar tube or cannula may be placed in the incision to facilitate the introduction and removal of surgical instrumentation. If further accessibility is required, a portion of the connective tissue and cartilage between the ribs may be removed to view the operative region and allow access for surgical instrumentation. In yet another alternative where more accessibility is required, one or more of the ribs may be cut adjacent the sternum and deflected. All of these methods of surgically accessing the region adjacent the heart may be less traumatic on the patient than the conventional medial sternotomy. The term "surgical access opening" will be used throughout the following description and will refer to any of the preceding minimally invasive access means deemed appropriate by the physician for the particular procedure and patient history. If necessary, a viewing scope, such as a thoracoscope, may be inserted through incision to assist in observing the procedure as it is carried out as described below. In addition, apparatus for sucking fluid, such as blood, from the operative site, may be inserted in the surgical access opening, e.g., to control bleeding.

FIG. 20 illustrates the aorta 20, which preferably serves as the existing body conduit and the arterial blood source in the exemplary embodiment. Coronary arteries 22 and 24 are at least partially blocked by occlusions or lesions 26 and 28, respectively. A graft conduit 30 has been installed according to the invention. The end portion of the graft conduit has been secured to the aorta 20 with a connector 200. The other end portion of the graft conduit has been secured to the coronary artery 22 downstream of the occlusion 26 by sutures 32.

Figure 21:
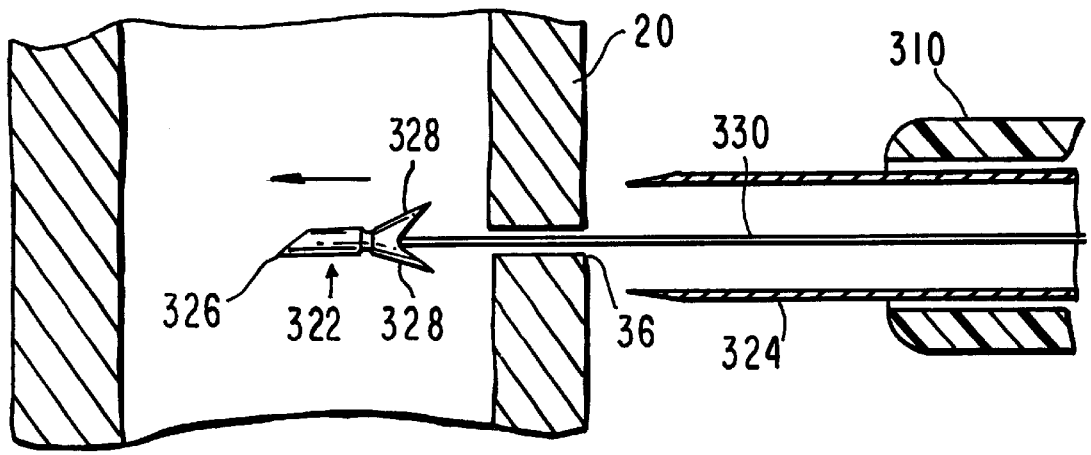
FIG. 21 is an enlarged sectional view of an early stage in the use of the FIG. 16 apparatus, in accordance with the invention.

The physician determines the location 36 on the aorta 20 for creating the anastomosis. The physician may grasp apparatus 100 by the proximal handle portion 110. The distal portion 130 is positioned adjacent location 36. More particularly, cutting mechanism 132 is used to make an opening in the aorta 20. The physician may depress plunger mechanism 114 in order to extend the stylet 322 distally. As illustrated in FIG. 21, the tip 326 pierces the tissue of aorta 20 at location 36 in the direction indicated by the arrow. The barbs 328 extend proximally and pass through the wall of the aorta 20.

Figure 22:
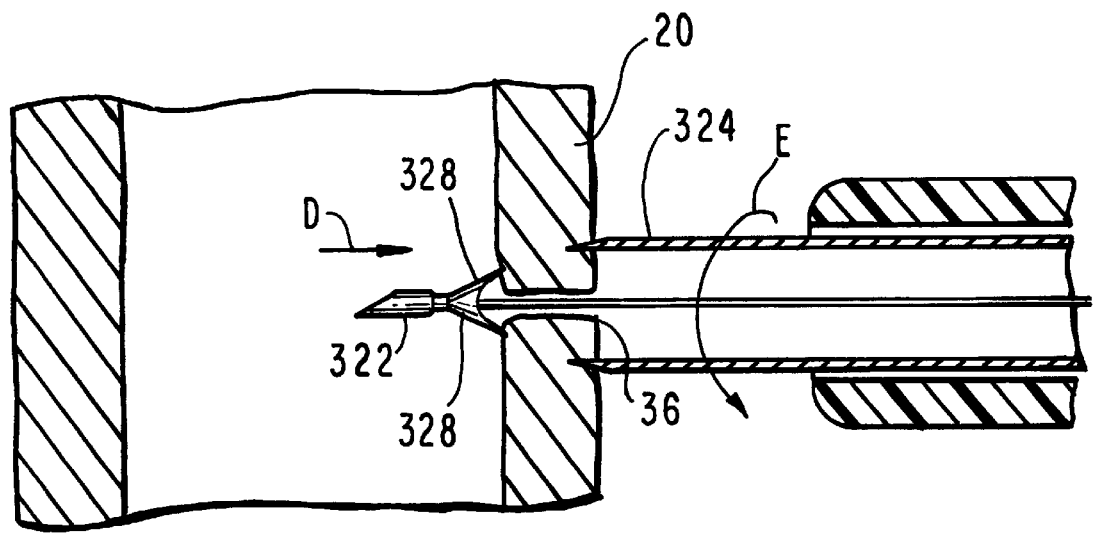
FIG. 22 is a sectional view, similar to FIG. 21, of a later stage in the use of the FIG. 16 apparatus, in accordance with the invention.

Once the stylet 322 has passed into the tissue, the physician may release the plunger mechanism 114, which retracts the stylet 322 proximally (as indicated by arrow D) in response to the spring bias described above. Consequently, the aorta wall is trapped between the barbs 328 of the stylet and the leading edge of the coring tip 324 (FIG. 22). The coring tip 324 is rotated about the longitudinal axis (as indicated by arrow E) and/or advanced distally in order to cut through the tissue.

Figure 23:
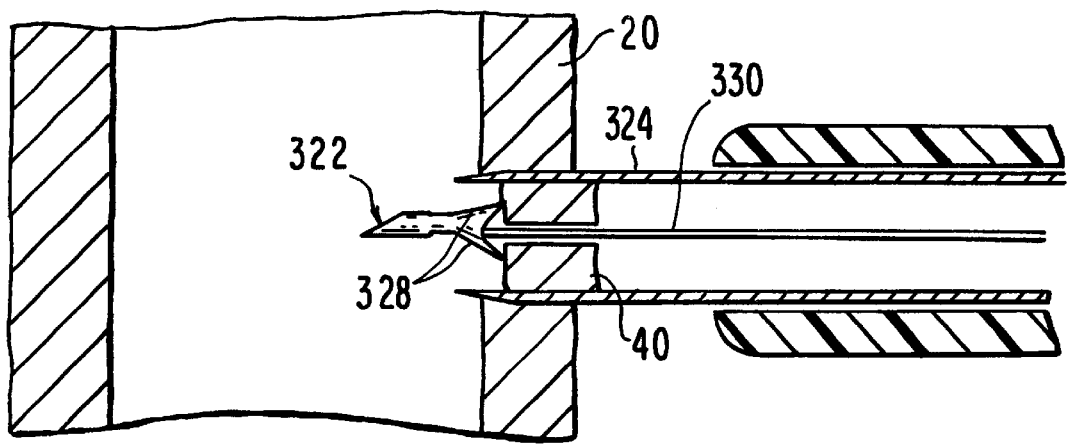
FIG. 23 is a sectional view, similar to FIG. 22, of a subsequent stage in the use of the FIG. 16 apparatus, in accordance with the invention.
Figure 24:
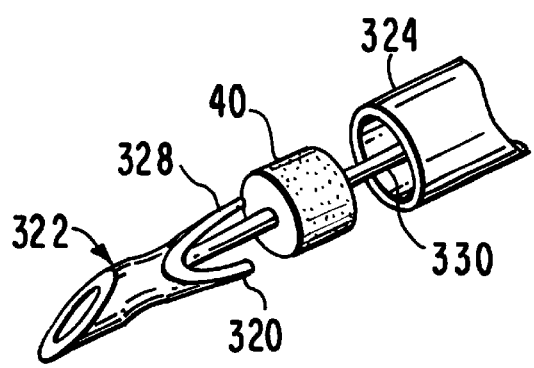
FIG. 24 is a perspective view of a still later stage in the use of the FIG. 16 apparatus, in accordance with the invention.

Once the coring tip 324 has cut through the aorta 20 (FIGS. 23 and 24), a plug of material 40 results from such cutting. The barbs 328 retain the plug 40 on the support member 330 and prevent the plug 40 from entering the bloodstream. It is also contemplated that cutting apparatus 420 may be used to cut the plug 40 from the aorta 20.

An alternative embodiment of the cutting mechanism is described herein. The apparatus and procedures are substantially identical to those described above with respect to FIGS. 16–24, above, with the substantial differences described herein. This alternative embodiment may be useful where the body conduit receiving the anastomosis is a smaller diameter vessel, such as, e.g., coronary artery 24.

Figure 25:
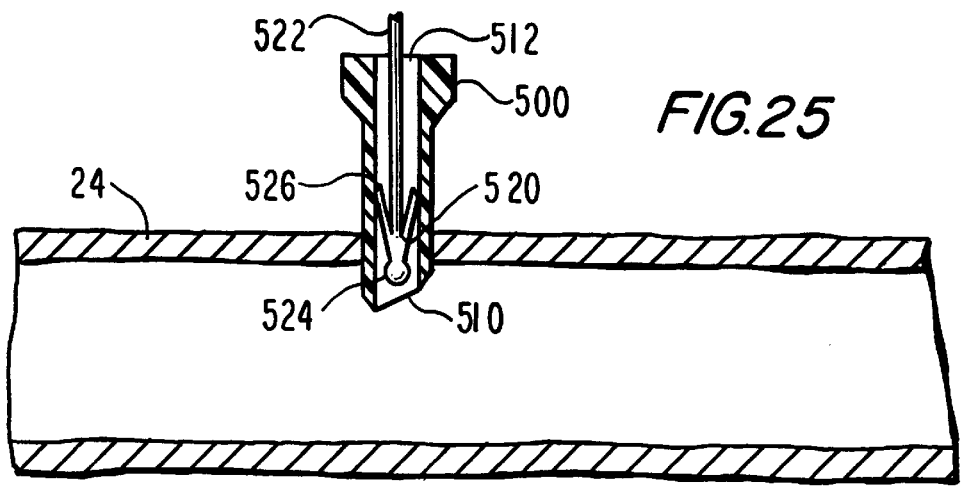
FIG. 25 is a sectional view of an early stage in the use of an alternative embodiment of the FIG. 16 apparatus, in accordance with the invention.
Figure 26:
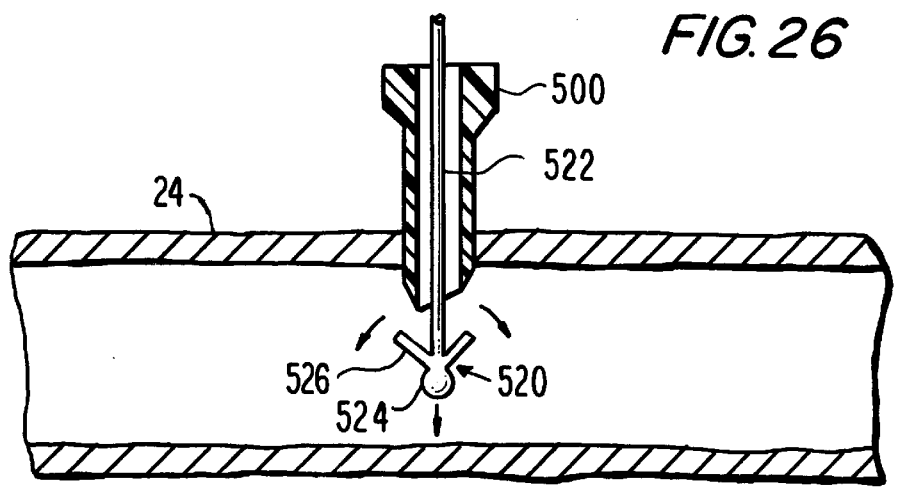
FIG. 26 is a sectional view similar to FIG. 25, illustrating a later stage in the use of the alternative embodiment of the apparatus, in accordance with the invention.

As illustrated in FIG. 25, the tissue holding structure may include a distal piercing portion, such as cannula needle 500, having a sharpened tip 510, to create an initial incision in the wall of the coronary artery 24. The tissue holding structure also includes a barb support member 520 disposed at the distal end portion of a catheter 522. The barb support member 520 is provided with an atraumatic bulb tip 524, which will not damage the interior wall of the vessel. The barb support member 520 is also provided with a pair of proximal barbs 526. The barbs 526 are resilient, such that while inside the lumen 512 of the cannula needle 500, the barbs are disposed in a retracted configuration towards parallelism with the longitudinal axis of the apparatus. The barb support member 520 is advanced into the vessel, whereupon the barbs 526 may resiliently extend radially outwards, as indicated by the arrows (FIG. 26).

Figure 27:
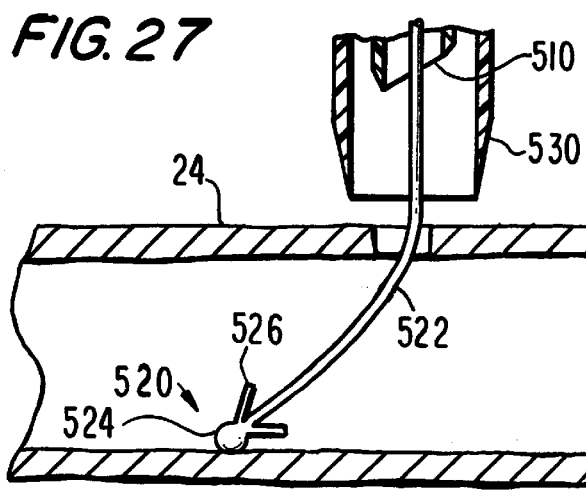
FIG. 27 is a sectional view similar to FIG. 26, illustrating a still later stage in the use of the alternative embodiment of the apparatus, in accordance with the invention.
Figure 28:
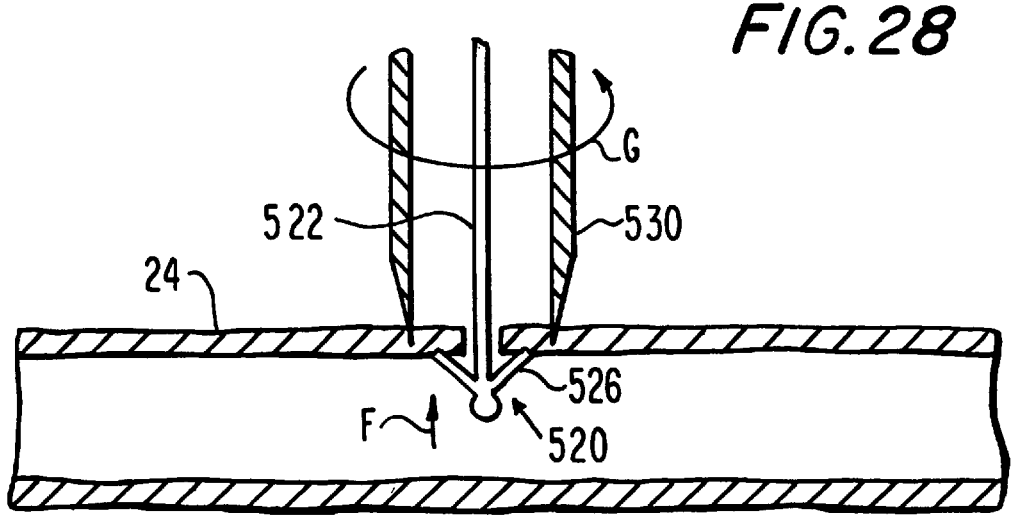
FIG. 28 is a sectional view similar to FIG. 27, illustrating a further stage in the use of the alternative embodiment of the apparatus, in accordance with the invention.
Figure 29:
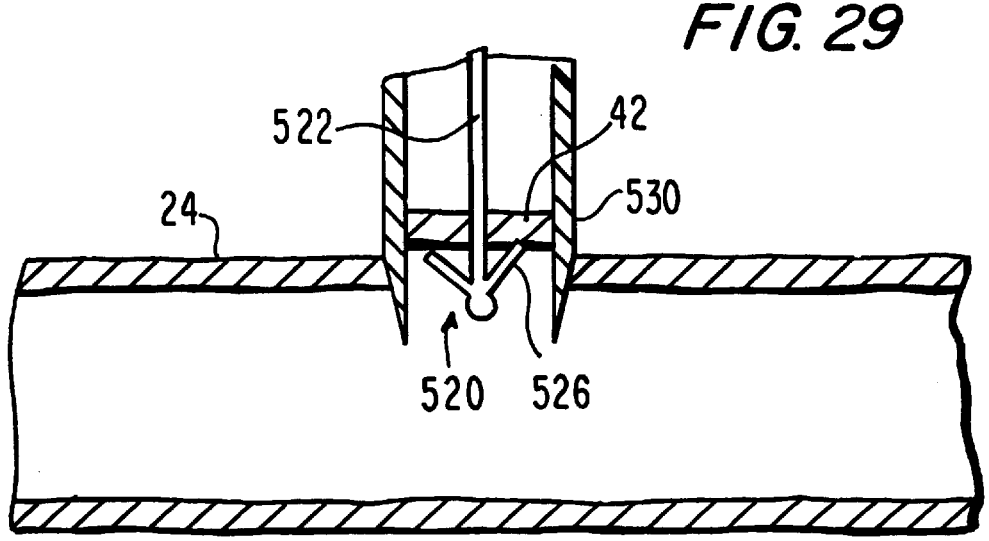
FIG. 29 is a sectional view similar to FIG. 28, illustrating a subsequent stage in the use of the alternative embodiment of the apparatus, in accordance with the invention.

The cannula needle 500 may be retracted proximally from the coronary artery 24. A coring tip 530, similar to the coring tip 324, described above, is advanced distally to the outer surface of the wall of the coronary artery 24 (FIG. 27). As illustrated in FIG. 28, the barb support member 520 is retracted proximally, preferably by withdrawing the catheter 522 (as indicated by arrow F). The wall of the coronary artery is trapped between the barbs 526 and the coring tip 530. The coring tip 530 is rotated about the longitudinal axis (as indicated by arrow G) and advanced distally into the coronary artery wall in order to cut the section 42 to be removed. Further advancement of coring tip 530 into the wall of the coronary artery 24 removes the section 42 as a cylindrical plug section. Barbs 526 retain the plug 42 inside the coring tip 530 and prevent the plug 42 from entering the bloodstream (FIG. 29).

Figure 30:
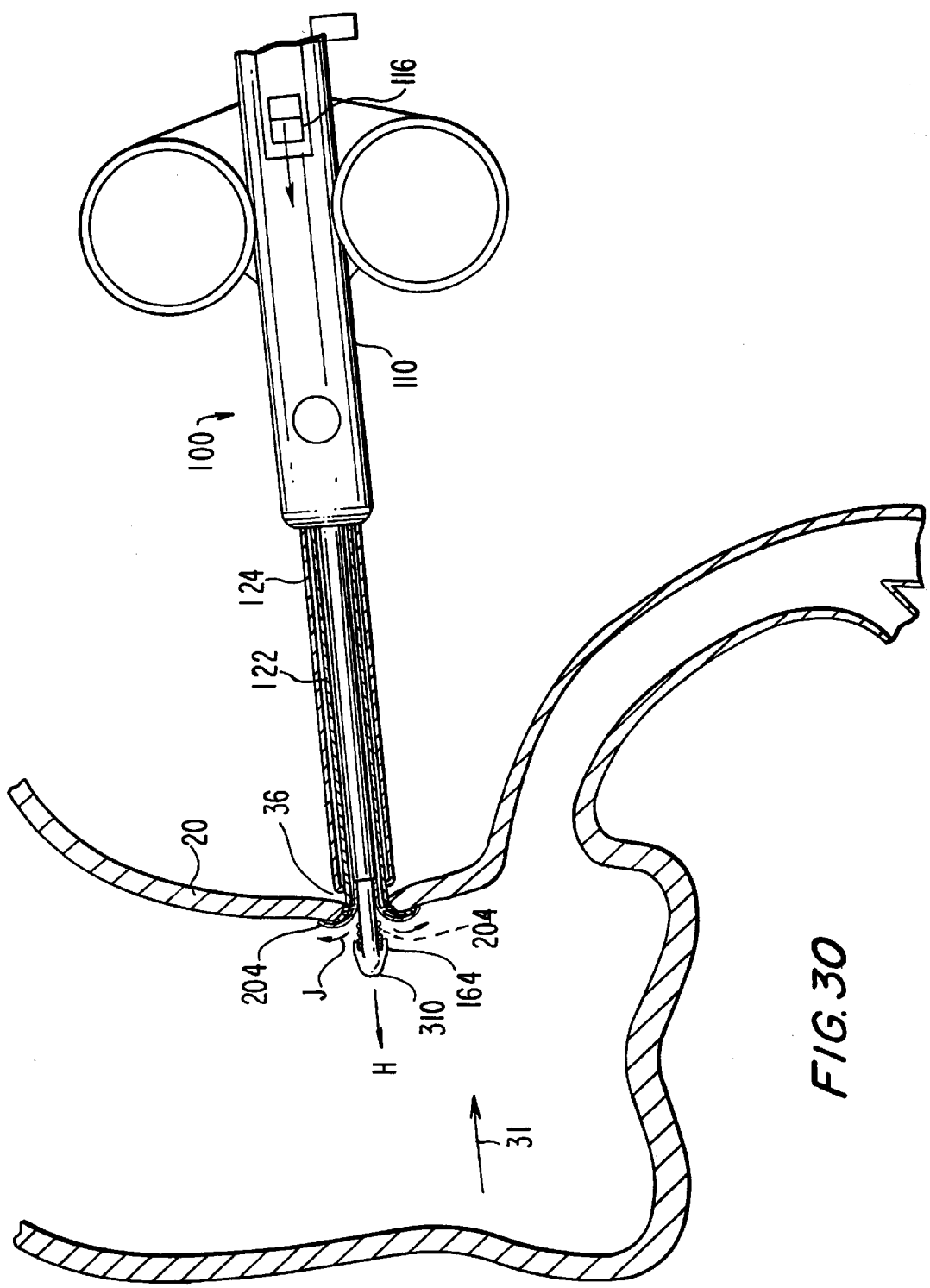
FIG. 30 is a simplified sectional view of a later stage in the use of the FIG. 16 apparatus, in accordance with the invention.
Figure 31:
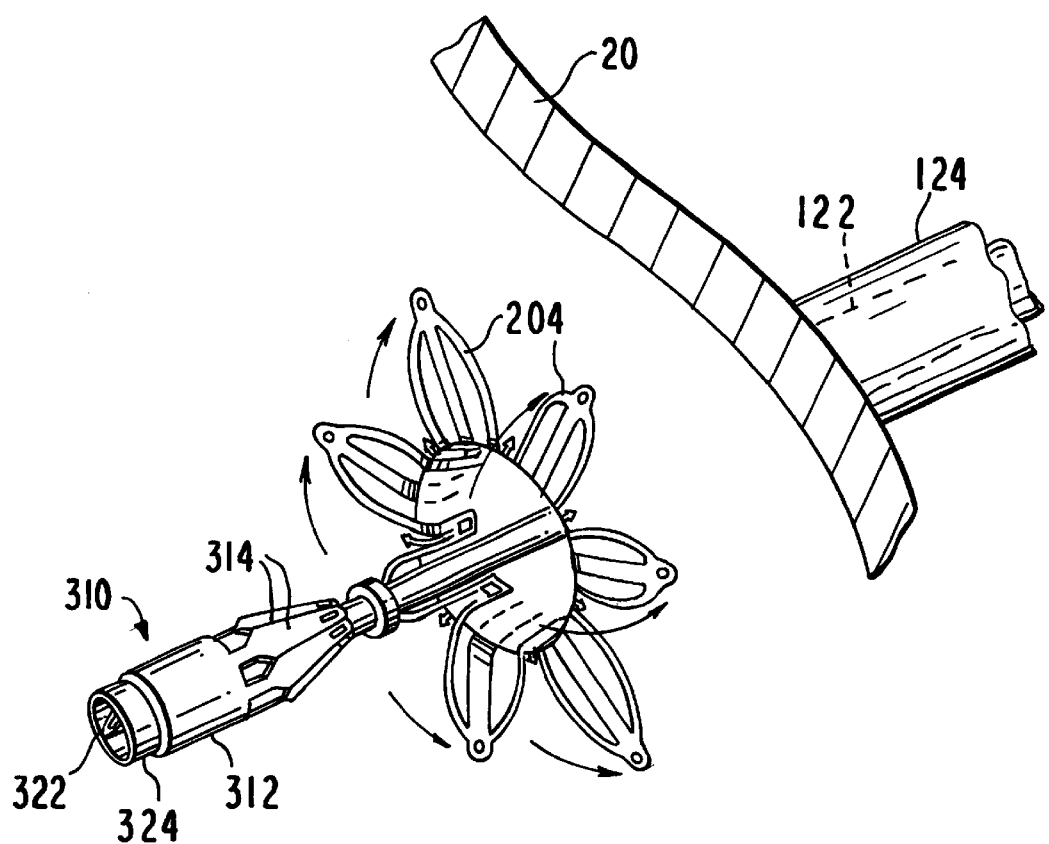
FIG. 31 is an enlarged perspective view from direction 31 of FIG. 30, at a still later stage, in accordance with the invention.

As illustrated in FIGS. 30 and 31, the distal portion 130 of apparatus 100 is advanced further into the aorta through the aperture created at location 36 by the cutting mechanism 132. (The details of the cutting mechanism have been omitted in order to simplify the ensuing discussion.) More particularly, nosecone 310 and annular sleeve 164, which retains internal members 204, are inserted into the lumen of the aorta 20. The physician may subsequently advance the inner retention member 162, and annular sleeve 164 and nosecone 310 therewith (as indicated by arrow H), while maintaining the support member 152 and the outer retention member 160 stationary. This is preferably accomplished by an actuation member, such as slide control 116 on the proximal handle portion 110.

Advancement of the inner retention member 162 and its annular sleeve 164 permits the internal fingers 204 to expand radially outwardly from the retained configuration (illustrated in dashed line) to the expanded position, as indicated by arrow J. FIG. 31 illustrates the radially outward expansion of fingers 204 in greater detail. Moreover, once the nosecone 310 has been advanced distally beyond the internal fingers 204, the leaves 314 of the nosecone 310 resiliently approximate radially inwardly. This assists in subsequently removing the distal portion 130 of apparatus 100 from the aorta after the connector 200 has been deployed, as will be described below.

Figure 32:
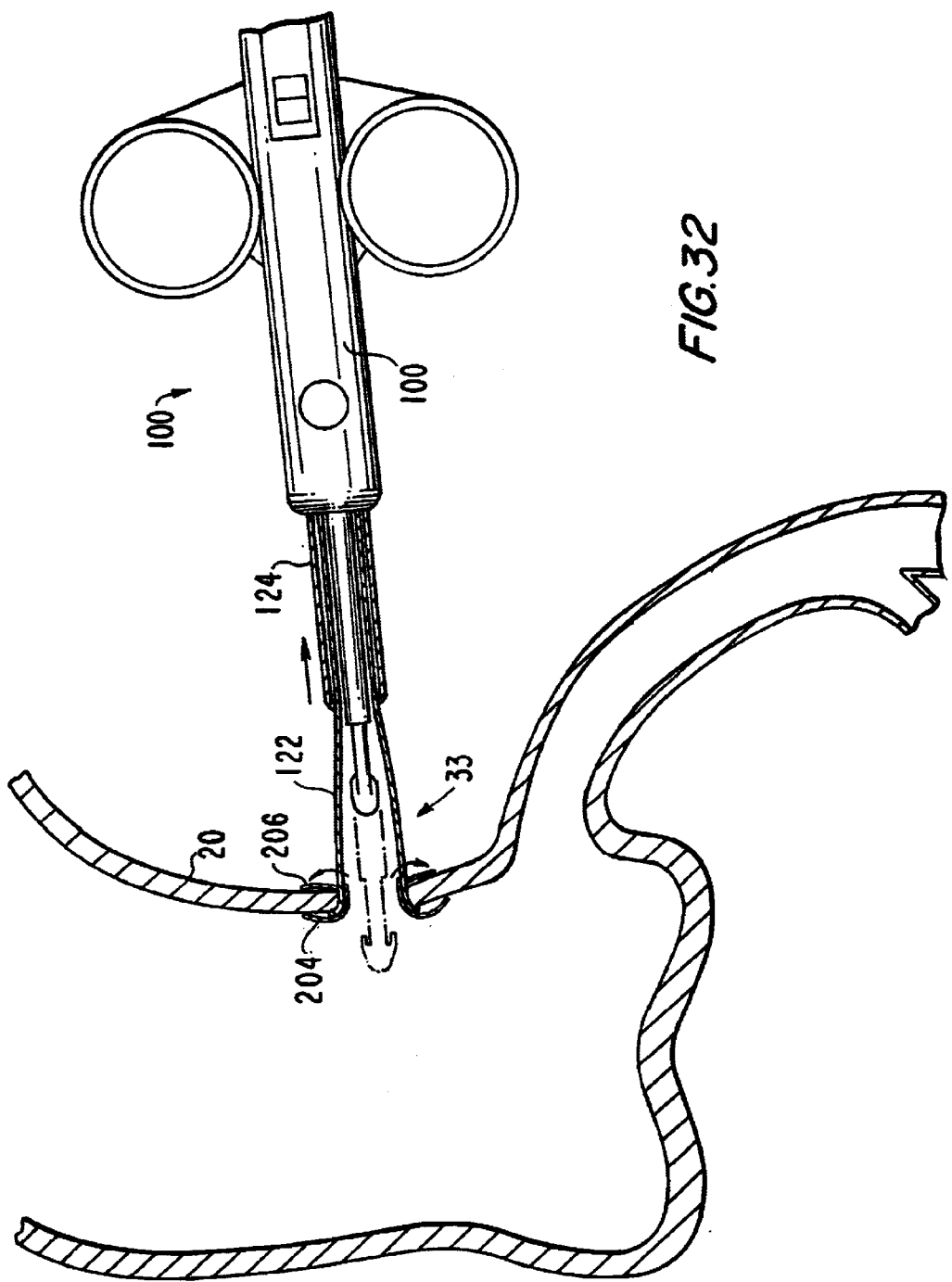
FIG. 32 is a simplified sectional view of a further stage in the use of the FIG. 16 apparatus, in accordance with the invention.
Figure 33:
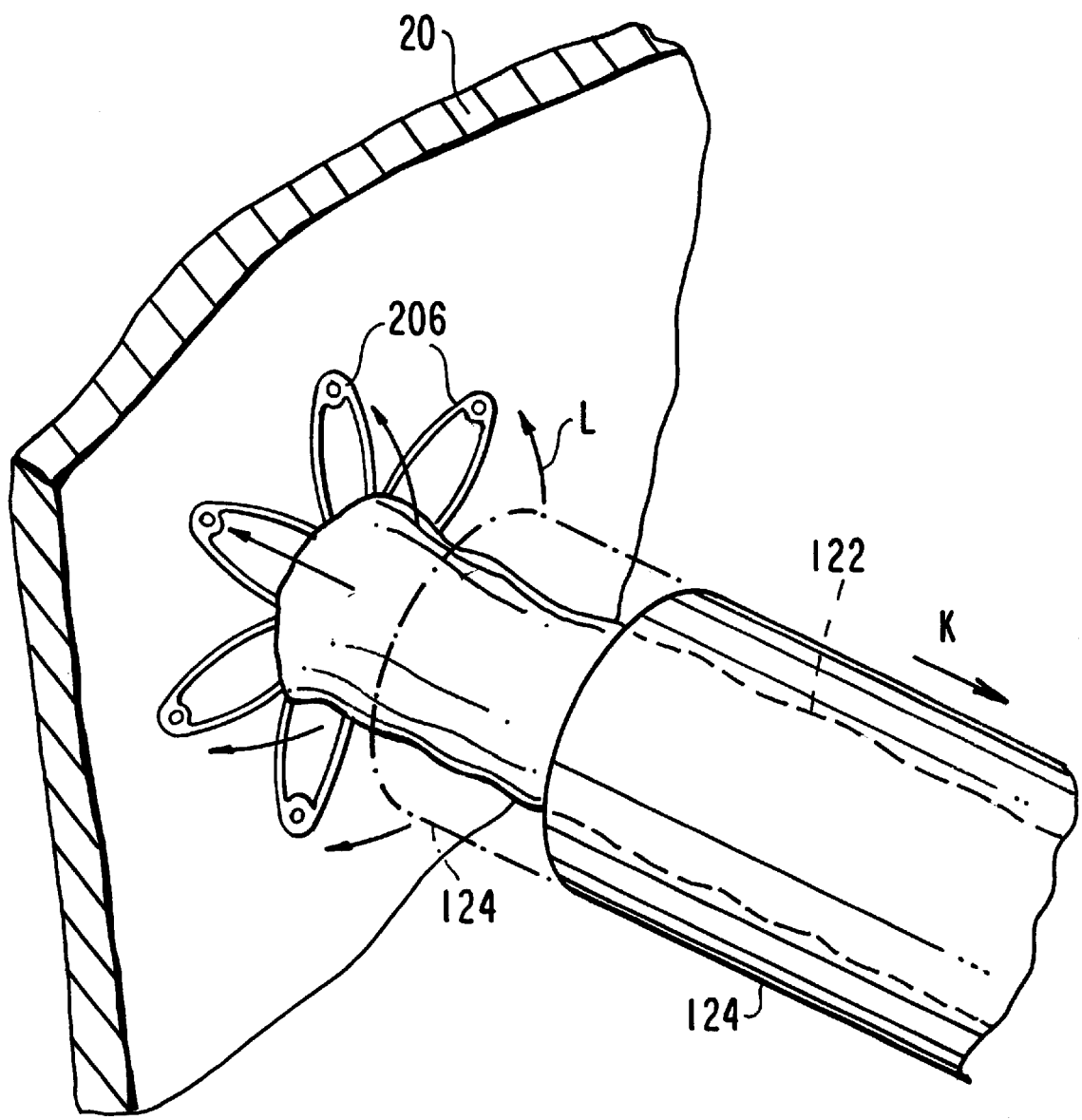
FIG. 33 is an enlarged perspective view from direction 33 of FIG. 32, in accordance with the invention.

The external fingers 206 may be subsequently deployed (FIGS. 32 and 33). As illustrated in FIG. 33, the delivery sheath 124, which retains external fingers in their backwardly deflected positioned, is retracted proximally from its position adjacent the aorta 20 (illustrated in dashed line) to a position spaced further apart, in the direction indicated by arrow K. This permits the external fingers 206 to resiliently expand radially outwardly and contact the external surface of the aorta 20 (in the direction indicated by arrows L).

Figure 34:
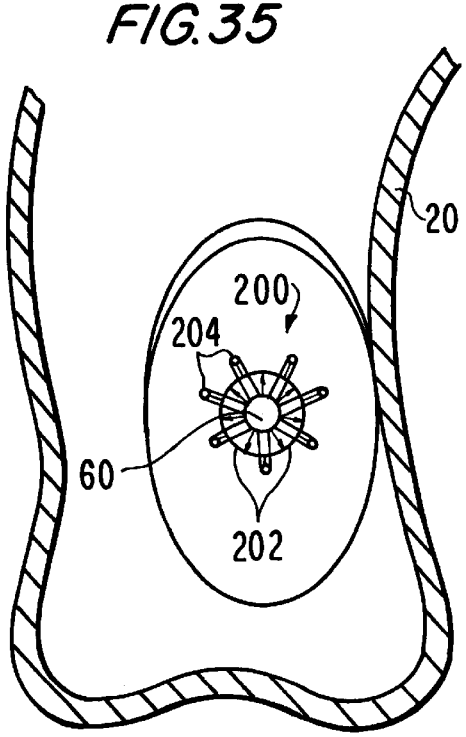
FIG. 34 is a simplified sectional view illustrating a still later stage in the installation of the connector apparatus and graft conduit, in accordance with the invention.
Figure 35:
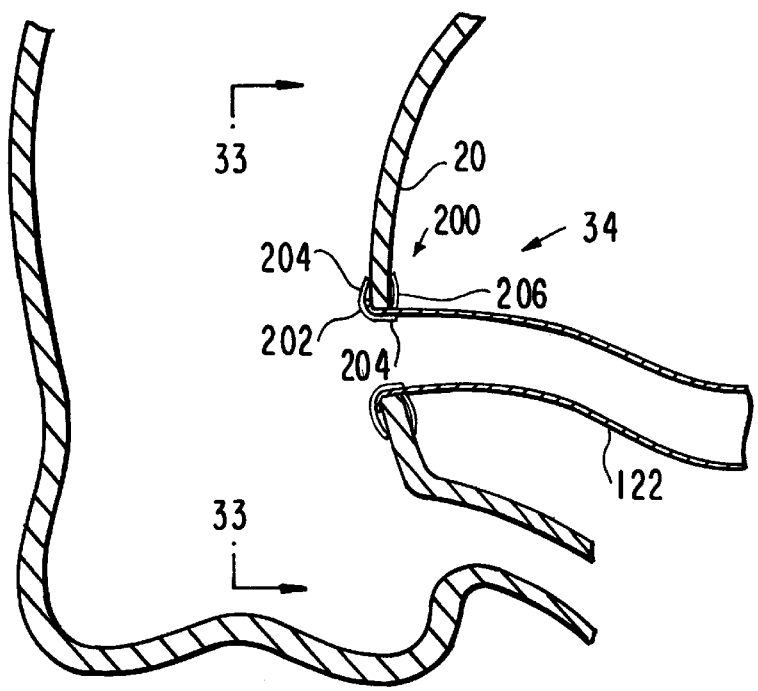
FIG. 35 is a simplified sectional view from line 33—33 of FIG. 34, in accordance with the invention.
Figure 36:
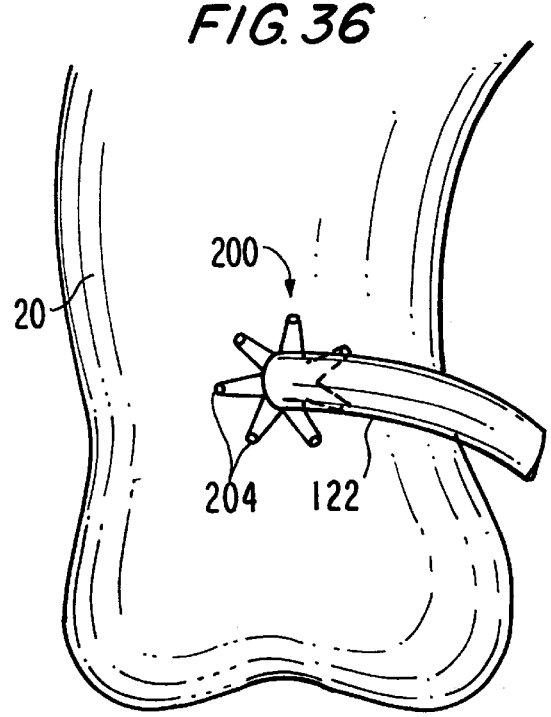
FIG. 36 is a simplified view from direction 34 of FIG. 34, in accordance with the invention.
Figure 37:
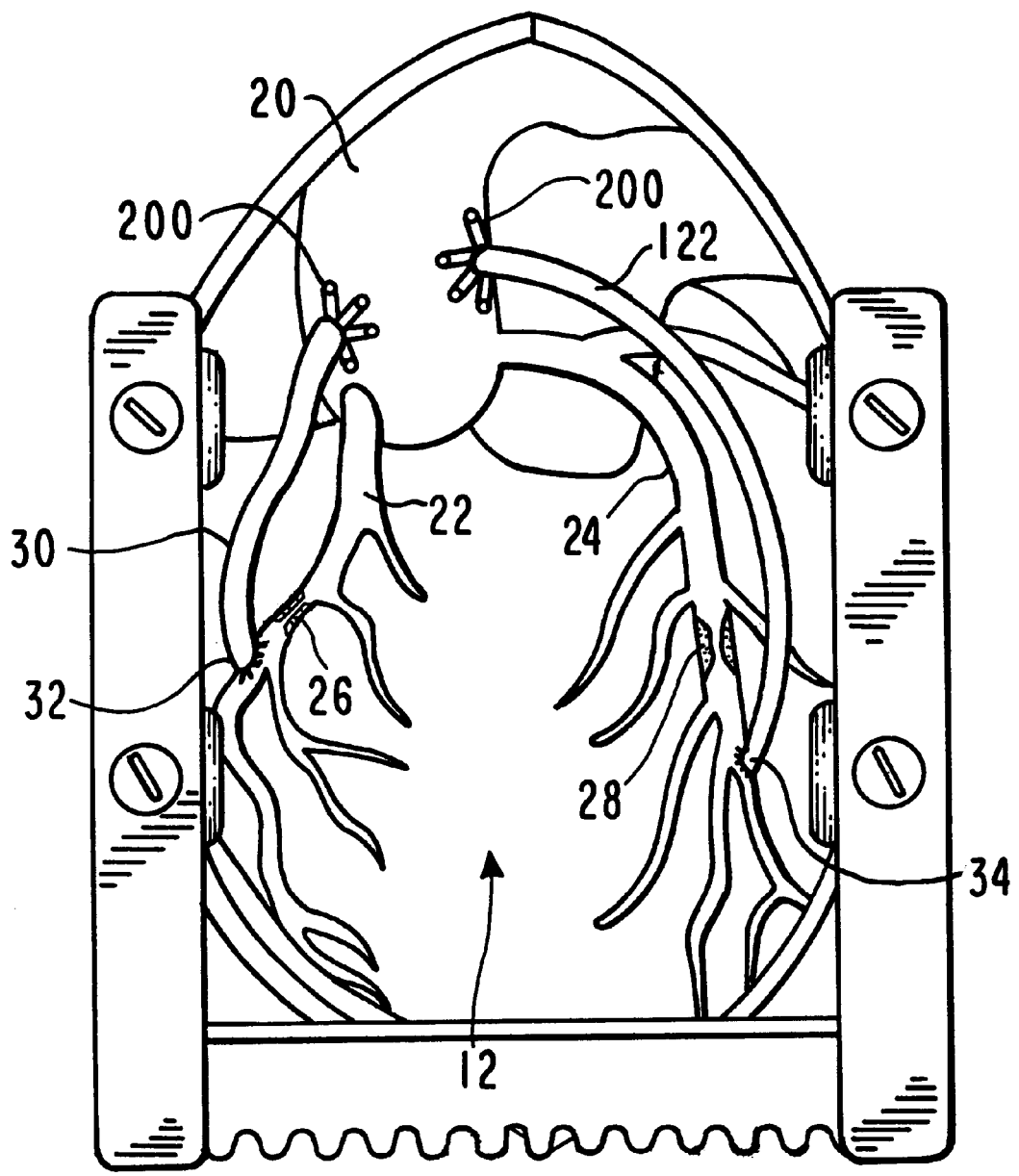
FIG. 37 is a simplified view similar to FIG. 20, illustrating a final stage in the procedure, in accordance with the invention.

The anastomosis is complete, and apparatus 100 is subsequently removed from the operative site (FIG. 34). As illustrated in FIG. 35 and 36, the connector 200 creates a substantially circular opening 60, which promotes smooth blood flow and rapid healing. The free end portion of the graft conduit 122 is subsequently attached to the coronary artery 24 (FIG. 37). It is contemplated that several methods may be used to make the attachment, such as sutures 34.

It will be understood that the foregoing is only illustrative of the principles of the invention and that various modifications can be made by those skilled in the art without departing from the scope and spirit of the invention. For example, the invention can be used to add a graft to the patient's circulatory system elsewhere than between the aorta and a coronary artery as has been specifically shown and described above.

What is claimed is:

1. Instrumentation for facilitating cutting an opening in a side wall of a body conduit comprising:

a tubular structure defining a lumen and having a sharpened distal end portion configured to cut a section of the body conduit to create the opening; and a tissue holding structure axially movable within the lumen of the tubular structure, the tissue holding structure comprising a piercing portion to permit passage of the tissue holding structure through the body conduit from an entrance side adjacent the tubular structure to an exit side thereof, and a retention member to secure the section of the body conduit to the tissue holding structure during movement of the tissue holding structure to approximate the entrance side of the section of the body conduit and the sharpened distal portion of the tubular structure which cuts the section of body conduit, wherein the retention member is a barb that is resiliently biased radially outwardly in order to secure the section of body conduit, wherein the barb is deflected radially inwardly during the distal passage of the tissue holding structure through the section of the body conduit, and wherein the piercing portion comprises a needle catheter having a sharpened distal end portion to permit passage of the tissue holding structure through the section of body conduit.

2. The instrumentation as defined in claim 1, wherein the tissue holding structure further comprises a barb support member which supports the barb thereon and is axially movable within an internal lumen of the needle catheter.

3. The instrumentation as defined in claim 2, wherein the needle catheter is sized to deflect the barb radially inwardly during distal movement of the barb support member through the internal lumen of the needle catheter, and which allows the barb to return to an outwardly extending orientation after passage through the internal lumen.

4. The instrumentation as defined in claim 2, wherein the barb support member has an atraumatic distal tip portion.

5. The instrumentation as defined in claim 2, wherein the barb support member extends distally from a flexible catheter.

6. Instrumentation for facilitating cutting an opening in a side wall of a body conduit comprising:
  a tubular structure defining a lumen and having a sharpened distal end portion configured to cut a section of the body conduit to create the opening;
  a tissue holding structure axially movable within the lumen of the tubular structure, the tissue holding structure comprising a piercing portion to permit passage of the tissue holding structure through the body conduit from an entrance side adjacent the tubular structure to an exit side thereof, and a retention member to secure the section of the body conduit to the tissue holding structure during movement of the tissue holding structure to approximate the entrance side of the section of the body conduit and the sharpened distal portion of the tubular structure which cuts the section of body conduit, wherein the retention member is a barb that is resiliently biased radially outwardly in order to secure the section of body conduit; and
  a connector for providing an anastomosis between the body conduit and a new length of body tubing comprising a first plurality of fingers for engaging an inner wall of the body conduit, a second plurality of fingers for engaging an outer wall of the body conduit, and a plurality of engagement members for securing the new length of body tubing to the connector.

7. The instrumentation as defined in claim 6, wherein the first plurality of fingers, the second plurality of fingers, and the engagement members are resiliently disposed radially outward.

8. The instrumentation as defined in claim 7, further comprising:
  a connector support defining a longitudinal axis and having a first retention structure to retain the first plurality of fingers towards parallelism with the longitudinal axis and a second retention structure to retain the second plurality of fingers towards parallelism with the longitudinal axis, such that the engagement members are disposed radially outwardly to facilitate attachment of the new length of tubing thereto by piercing the new length of tubing.

9. The instrumentation as defined in claim 8, wherein the connector support defines an interior lumen for receiving the tubular structure and tissue holding structure therethrough.

10. The instrumentation as defined in claim 8, wherein the first retention structure is an annular sleeve for retaining the first plurality of fingers distally towards parallelism with the longitudinal axis.

11. The instrumentation as defined in claim 10, wherein the first retention structure retains the first plurality of fingers in a configuration having a dimension smaller than the opening in the body conduit.

12. The instrumentation as defined in claim 8, wherein the second retention structure is an annular sleeve to retain the second plurality of fingers towards parallelism with the longitudinal axis.

13. Instrumentation for facilitating cutting an opening in a side wall of a body conduit comprising:
  a tubular structure defining a lumen and having a sharpened distal end portion configured to cut a section of the body conduit to create the opening;
  a tissue holding structure axially movable within the lumen of the tubular structure, the tissue holding structure comprising a piercing portion to permit passage of the tissue holding structure through the body conduit from an entrance side adjacent the tubular structure to an exit side thereof, and a retention member to secure the section of the body conduit to the tissue holding structure during movement of the tissue holding structure to approximate the entrance side of the section of the body conduit and the sharpened distal portion of the tubular structure which cuts the section of body conduit;
  a connector for providing an anastomosis between the body conduit and a new length of body tubing comprising a first plurality of fingers for engaging an inner wall of the body conduit, a second plurality of fingers for engaging an outer wall of the body conduit, and a plurality of engagement members for securing the new length of body tubing to the connector, wherein the first plurality of fingers, the second plurality of fingers, and the engagement members are resiliently disposed radially outward; and
  a connector support defining a longitudinal axis and having a first retention structure to retain the first plurality of fingers towards parallelism with the longitudinal axis and a second retention structure to retain the second plurality of fingers towards parallelism with the longitudinal axis, such that the engagement members are disposed radially outwardly to facilitate attachment of the new length of tubing thereto by piercing the new length of tubing, wherein the second retention structure is a member having a projection received in a corresponding opening in each of the second plurality of fingers to retain the second plurality of fingers towards parallelism with the longitudinal axis.

14. Instrumentation for facilitating cutting an opening in a side wall of a body conduit comprising:
  a tubular structure defining a lumen and having a sharpened distal end portion configured to cut a section of the body conduit to create the opening;

a tissue holding structure axially movable within the lumen of the tubular structure, the tissue holding structure comprising a piercing portion to permit passage of the tissue holding structure through the body conduit from an entrance side adjacent the tubular structure to an exit side thereof, and a retention member to secure the section of the body conduit to the tissue holding structure during movement of the tissue holding structure to approximate the entrance side of the section of the body conduit and the sharpened distal portion of the tubular structure which cuts the section of body conduit;

a connector for providing an anastomosis between the body conduit and a new length of body tubing comprising a first plurality of fingers for engaging an inner wall of the body conduit, a second plurality of fingers for engaging an outer wall of the body conduit, and a plurality of engagement members for securing the new length of body tubing to the connector, wherein the new length of tubing has a direction of natural fluid flow; and a sleeve sized for passage within the new length of tubing having a tapered tip portion to provide a visual indication of the direction of natural fluid flow.

15. Instrumentation for facilitating cutting an opening in a side wall of a body conduit comprising:

a tubular structure defining a lumen and having a sharpened distal end portion configured to cut a section of the body conduit to create the opening;

a tissue holding structure axially movable within the lumen of the tubular structure, the tissue holding structure comprising a piercing portion to permit passage of the tissue holding structure through the body conduit from an entrance side adjacent the tubular structure to an exit side thereof, and a retention member to secure the section of the body conduit to the tissue holding structure during movement of the tissue holding structure to approximate the entrance side of the section of the body conduit and the sharpened distal portion of the tubular structure which cuts the section of body conduit;

a connector for providing an anastomosis between the body conduit and a new length of body tubing comprising a first plurality of fingers for engaging an inner wall of the body conduit, a second plurality of fingers for engaging an outer wall of the body conduit, and a plurality of engagement members for securing the new length of body tubing to the connector, wherein the first plurality of fingers, the second plurality of fingers, and the engagement members are resiliently disposed radially outward;

a connector support defining a longitudinal axis and having a first retention structure to retain the first plurality of fingers towards parallelism with the longitudinal axis and a second retention structure to retain the second plurality of fingers towards parallelism with the longitudinal axis, such that the engagement members are disposed radially outwardly to facilitate attachment of the new length of tubing thereto by piercing the new length of tubing; and a pressure-application tool for facilitating the piercing of the new length of tubing by individual ones of the engagement members to secure the new length of tubing to the, connector, the pressure-application tool having a distal sleeve portion with an internal lumen sized such that individual ones of the engagement members may be received therein, the sleeve providing substantially uniform pressure to the new length of tubing about the engagement member to pierce the new length of tubing by the engagement member.

16. A method for cutting an opening in a body conduit comprising:

providing a tissue holding structure having a retention member to secure a section of the body conduit to the tissue holding structure;

securing the retention member to the section of the body conduit by at least partially inserting the tissue holding structure into the body conduit;

providing a tubular structure having a sharpened distal portion;

approximating the body conduit and the sharpened distal portion of the tubular structure by relative movement of the tissue holding structure towards the tubular structure; and cutting the section of the body conduit with the sharpened distal portion of the tubular structure to provide the opening in the body conduit, wherein the tissue holding structure further comprises a piercing portion, wherein securing the retention member to the body conduit comprises piercing the body conduit with the piercing portion of the tissue holding structure, wherein the piercing portion comprises a needle catheter having a sharpened distal end portion, and wherein piercing the body conduit comprises piercing the body conduit from an entrance side to an exit side with the needle catheter.

17. A method for cutting an opening in a body conduit comprising:

providing a tissue holding structure having a retention member to secure a section of the body conduit to the tissue holding structure;

securing the retention member to the section of the body conduit by at least partially inserting the tissue holding structure into the body conduit;

providing a tubular structure having a sharpened distal portion;

approximating the body conduit and the sharpened distal portion of the tubular structure by relative movement of the tissue holding structure towards the tubular structure; and cutting the section of the body conduit with the sharpened distal portion of the tubular structure to provide the opening in the body conduit, wherein the tissue holding structure further comprises a piercing portion, wherein securing the retention member to the body conduit comprises piercing the body conduit with the piercing portion of the tissue holding structure, wherein the piercing portion comprises a needle catheter having a sharpened distal end portion, wherein piercing the body conduit comprises piercing the body conduit from an entrance side to an exit side with the needle catheter, wherein the tissue holding structure further comprises a barb support member which supports a barb thereon and is axially movable within an internal lumen of the needle catheter, and wherein the securing further comprises passing the barb support member and the barb through the internal lumen of the needle catheter from the entrance side to the exit side.

18. The method as defined in claim 17, wherein the needle catheter is sized to deflect the barb radially inwardly during distal movement of the barb support member through the internal lumen of the needle catheter.

19. The method as defined in claim 18, wherein the securing the retention member to the body conduit further comprises allowing the barb to return to a configuration wherein the retention member is positioned radially outwardly in order to secure the body conduit thereby.

20. The method as defined in claim 17, wherein the barb support member extends distally from a flexible catheter and
wherein securing the tissue holding member to the body conduit further comprises advancing the catheter towards the body conduit.

21. The method as defined in claim 20, wherein the approximating the body conduit and the sharpened portion of the tubular structure comprises withdrawing the catheter away from the body conduit.

22. A method for performing an anastomosis between a body conduit and a new length of tubing comprising:
providing a tissue holding structure having a retention member to secure a section of the body conduit to the tissue holding structure;
securing the retention member to the section of the body conduit by at least partially inserting the tissue holding structure into the body conduit;
providing a tubular structure having a sharpened distal portion;
approximating the body conduit and the sharpened distal portion of the tubular structure by relative movement of the tissue holding structure towards the tubular structure;
cutting the section of the body conduit with the sharpened distal portion of the tubular body structure to provide an opening in the body conduit; and
attaching the new length of tubing to the body conduit adjacent the opening made by the cutting.

23. The method as defined in claim 22, further comprising:
providing a connector defining a central opening and comprising a first plurality of fingers for engaging an inner wall of the body conduit, a second plurality of fingers for engaging an outer wall of the body conduit, and a plurality of engagement members for securing a portion of the new length of body tubing to the connector, wherein attaching the new length of tubing to the body conduit adjacent the opening comprises securing a portion of the new length of body tubing to the connector with the plurality of engagement members, engaging the inner wall of the body conduit with the first plurality of fingers, and engaging the outer wall of the body conduit with the second plurality of fingers.

24. The method as defined in claim 23, further comprising:
providing a connector support defining a longitudinal axis and having a first retention structure for retaining at least one finger of the first plurality of fingers towards parallelism with the longitudinal axis; and
prior to securing the portion of the new length of tubing to the connector, mounting the connector coaxially about the connector support and retaining the at least one finger of the first plurality of fingers with the retention structure.

25. The method as defined in claim 24, wherein the connector support further comprises a second retention structure such that the engagement members are disposed radially outwardly to facilitate attachment of the new length of tubing thereto.

26. The method as defined in claim 25, wherein mounting the connector coaxially about the connector support further comprises retaining the first plurality of fingers towards parallelism with the longitudinal axis and retaining the second plurality of fingers towards parallelism with the longitudinal axis such that the engagement members are disposed radially outwardly to facilitate attachment of the new length of tubing thereto.

27. The method as defined in claim 26, wherein the first retention structure is an annular sleeve, and wherein mounting the connector coaxially about the connector support further comprises retaining the first plurality of fingers distally towards parallelism with the longitudinal axis.

28. The method as defined in claim 26, wherein the mounting the connector coaxially about the connector support further comprises retaining the first plurality of fingers in a configuration having a diameter smaller than the opening in the body conduit.

29. A method for performing an anastomosis between a body conduit and a new length of tubing comprising:
providing a tissue holding structure having a retention member to secure a section of the body conduit to the tissue holding structure;
securing the retention member to the section of the body conduit by at least partially inserting the tissue holding structure into the body conduit;
providing a tubular structure having a sharpened distal portion;
approximating the body conduit and the sharpened distal portion of the tubular structure by relative movement of the tissue holding structure towards the tubular structure;
cutting the section of the body conduit with the sharpened distal portion of the tubular body structure to provide an opening in the body conduit;
attaching the new length of tubing to the body conduit adjacent the opening made by the cutting;
providing a connector defining a central opening and comprising a first plurality of fingers for engaging an inner wall of the body conduit, a second plurality of fingers for engaging an outer wall of the body conduit, and a plurality of engagement members for securing a portion of the new length of body tubing to the connector, wherein attaching the new length of tubing to the body conduit adjacent the opening comprises securing a portion of the new length of body tubing to the connector with the plurality of engagement members, engaging the inner wall of the body conduit with the first plurality of fingers, and engaging the outer wall of the body conduit with the second plurality of fingers;
providing a connector support defining a longitudinal axis and having a first retention structure for retaining at least one finger of the first plurality of fingers towards parallelism with the longitudinal axis; and
prior to securing the portion of the new length of tubing to the connector, mounting the connector coaxially about the connector support and retaining the at least one finger of the first plurality of fingers with the retention structure, wherein the connector support further comprises a second retention structure such that the engagement members are disposed radially outwardly to facilitate attachment of the new length of tubing thereto, wherein mounting the connector coaxially about the connector support further comprises retaining the first plurality of fingers towards parallelism with the longitudinal axis and retaining the second plurality of fingers towards parallelism with the longitudinal axis such that the engagement members are disposed radially outwardly to facilitate attachment of the new length of tubing thereto, and wherein the second retention structure is a member having a tab received in a corresponding opening in each of the second plurality of fingers.

30. The method as defined in claim 29, wherein the member is a tubular sheath, the method further comprising:

after securing the new length of tubing to the connector, releasing the second plurality of fingers from the tabs and advancing the tubular sheath such that the second plurality of fingers are deflected towards parallelism with the longitudinal axis in a substantially opposite direction than prior to the releasing.

31. The method as defined in claim 30, wherein attaching the new length to tubing to the body conduit adjacent the opening further comprises:

inserting the first plurality of fingers into the opening;

releasing the first retention structure to allow the first plurality of fingers to engage the inner wall of the body conduit; and releasing the second retention structure to allow the second plurality of fingers to engage the outer wall of the body conduit.

32. A method for performing an anastomosis between a body conduit and a new length of tubing comprising:

providing a tissue holding structure having a retention member to secure a section of the body conduit to the tissue holding structure;

securing the retention member to the section of the body conduit by at least partially inserting the tissue holding structure into the body conduit;

providing a tubular structure having a sharpened distal portion;

approximating the body conduit and the sharpened distal portion of the tubular structure by relative movement of the tissue holding structure towards the tubular structure;

cutting the section of the body conduit with the sharpened distal portion of the tubular body structure to provide an opening in the body conduit;

attaching the new length of tubing to the body conduit adjacent the opening made by the cutting;

providing a connector defining a central opening and comprising a first plurality of fingers for engaging an inner wall of the body conduit, a second plurality of fingers for engaging an outer wall of the body conduit, and a plurality of engagement members for securing a portion of the new length of body tubing to the connector, wherein attaching the new length of tubing to the body conduit adjacent the opening comprises securing a portion of the new length of body tubing to the connector with the plurality of engagement members, engaging the inner wall of the body conduit with the first plurality of fingers, and engaging the outer wall of the body conduit with the second plurality of fingers, wherein the new length of tubing has a direction of natural fluid flow;

providing a sleeve sized for passage within the new length of tubing having a tapered tip portion to provide a visual indication of the direction of natural fluid flow; and before securing the portion of the new length of tubing to the connector, advancing the new length of tubing over the sleeve such that new length of tubing may be attached to the connector based on the direction of natural fluid flow.

33. A method for performing an anastomosis between a body conduit and a new length of tubing comprising:

providing a tissue holding structure having a retention member to secure a section of the body conduit to the tissue holding structure;

securing the retention member to the section of the body conduit by at least partially inserting the tissue holding structure into the body conduit;

providing a tubular structure having a sharpened distal portion;

approximating the body conduit and the sharpened distal portion of the tubular structure by relative movement of the tissue holding structure towards the tubular structure;

cutting the section of the body conduit with the sharpened distal portion of the tubular body structure to provide an opening in the body conduit;

attaching the new length of tubing to the body conduit adjacent the opening made by the cutting;

providing a connector defining a central opening and comprising a first plurality of fingers for engaging an inner wall of the body conduit, a second plurality of fingers for engaging an outer wall of the body conduit, and a plurality of engagement members for securing a portion of the new length of body tubing to the connector, wherein attaching the new length of tubing to the body conduit adjacent the opening comprises securing a portion of the new length of body tubing to the connector with the plurality of engagement members, engaging the inner wall of the body conduit with the first plurality of fingers, and engaging the outer wall of the body conduit with the second plurality of fingers; and providing a pressure-application tool having a distal sleeve portion with an internal lumen sized such that individual ones of the engagement members may be received therein, wherein securing the portion of the new length of tubing to the connector comprises providing substantially uniform pressure by the sleeve portion to the new length of tubing about the engagement member to facilitate piercing of the new length of tubing by the engagement member.

* * * * *